(12) United States Patent
Tappel et al.

(10) Patent No.: US 11,306,333 B2
(45) Date of Patent: Apr. 19, 2022

(54) WOOD-LJUNGDAHL MICROORGANISMS THAT PRODUCE POLYHYDROXYBUTYRATE

(71) Applicant: LanzaTech, Inc., Skokie, IL (US)

(72) Inventors: Ryan Christopher Tappel, Skokie, IL (US); James Bruce Yarnton Haycock Behrendorff, Copenhagen (DK); Michael Koepke, Skokie, IL (US); Esteban Marcellin, St. Lucia (AU); Renato de Souza Pinto Lemgruber, St. Lucia (AU); Kaspar Valgepea, St. Lucia (AU); Lars Nielsen, St. Lucia (AU)

(73) Assignee: LanzaTech, Inc., Skokie, IL (US)

( * ) Notice: Subject to any disclaimer, the term of this patent is extended or adjusted under 35 U.S.C. 154(b) by 0 days.

(21) Appl. No.: 16/152,354

(22) Filed: Oct. 4, 2018

(65) Prior Publication Data

US 2019/0119706 A1 Apr. 25, 2019

Related U.S. Application Data

(60) Provisional application No. 62/568,127, filed on Oct. 4, 2017.

(51) Int. Cl.
*C12P 7/62* (2006.01)
*C12N 9/10* (2006.01)
*C12N 9/04* (2006.01)
*C12P 7/625* (2022.01)

(52) U.S. Cl.
CPC ............ *C12P 7/625* (2013.01); *C12N 9/0006* (2013.01); *C12N 9/1029* (2013.01); *C12Y 101/01036* (2013.01); *C12Y 101/01157* (2013.01); *C12Y 203/01* (2013.01); *C12Y 203/01009* (2013.01)

(58) Field of Classification Search
None
See application file for complete search history.

(56) References Cited

U.S. PATENT DOCUMENTS

| | | | |
|---|---|---|---|
| 5,610,041 A | 3/1997 | Somerville | |
| 2005/0227340 A1 | 10/2005 | Kim | |
| 2009/0191593 A1* | 7/2009 | Burk | C12N 9/0008 435/75 |
| 2011/0201089 A1 | 8/2011 | Burgard | |

FOREIGN PATENT DOCUMENTS

WO 2011043829 A2 4/2011

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Hiroe et al. Applied and Environmental Microbiology Apr. 2012, 78 (9) 3177-3184 (Year: 2012).*
Mifune et al. Polymer Degradation and Stability 95 (2010) 1305-1312 (Year: 2010).*
Humphreys et al. BMC Genomics. Dec. 21, 2015;16:1085 (Year: 2015).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Abrini, Arch Microbiol, 161: 345-351, 1994.
Anjum, Int J Biol Macromol, 89: 161-174, 2016.
Biegel, Cell Mol Life Sci, 68: 613-634, 2011.
Brown, Biotechnol. Biofuels, 7: 40, 2014.
Chen, Appl Microbiol Biotechnol, 57: 50-55, 2001.
De Livera, Anal Chem, 84: 10768-10776, 2012.
De Livera, Metabolomics Tools for Natual Product Discovery, 2013.
Drake, Acetogenic Prokaryotes, In: The Prokaryotes, 3rd edition, p. 354, New York, NY, 2006.
Drzyzga, J Chem Technol Biotechnol, 90: 1735-1751, 2015.
Elbahloul, Appl Environ Microbiol, 75: 643-651, 2009.
Heap, J Microbiol Methods, 78: 79-85, 2009.
Heinrich, AMB Express, 2: 59, 2012.
Hungate, Methods in Microbiology, pp. 117-132, Academic Press, New York, NY, 1969.
Karr, Appl Environ Microbiol, 46, 1339-1344, 1983.
Köpke, Appl Environ Microbiol, 77: 5467-5475, 2011.
Köpke, Curr Opin Biotechnol, 22: 320-325, 2011.
Kunasundari, Express Polym Lett, 5, 620-634, 2011.
Marcellin, Green Chem, 18: 3020-3028, 2016.
Mock, J Bacteriol, 197:2965-2980, 2015.
Pohlmann, Nat Biotechnol, 24: 1257-1262, 2006.
Ragsdale, Biochim Biophys Acta, 1784: 1873-1898, 2008.
Schuchmann, Nat Rev Microbiol, 12: 809-821, 2014.
Valgepea, Cell Syst, 4: 505-515, 2017.
Valgepea, Metab Eng.,41: 202-211, 2017.
Wang, J Bacteriol, 195: 4373-4386, 2013.
Extended European Search Report issued in corresponding European Application No. 18865091.5, dated Jun. 1, 2021, 11 pages.
Mifune, J. et al. "Engineering of pha operon on Cupriavidus necator chromosome for efficient biosynthesis of poly (3-hydroxybutyrate-co-3-hydroxyhexanoate) from vegetable oil," Polymer Degradation and Stability, vol. 95, Issue 8, Aug. 2010, pp. 1305-1312.
Hiroe, Ayaka et al. "Rearrangement of Gene Order in the phaCAB Operon Leads to Effective Production of Ultrahigh-Molecular-Weight Poly[(R)-3-Hydroxybutyrate] in Genetically Engineered *Escherichia coli*," Applied and Environmental Microbiology, vol. 78, No. 9, Feb. 17, 2012, pp. 3177-3184.

* cited by examiner

*Primary Examiner* — Christian L Fronda
(74) *Attorney, Agent, or Firm* — Stephen M. Chong

(57) ABSTRACT

The invention provides microorganisms and methods for the production of polyhydroxybutyrate (PHB) from gaseous substrates. In particular, the invention provides a non-naturally occurring Wood-Ljungdahl microorganism comprising (a) an enzyme that converts acetyl-CoA to acetoacetyl-CoA, (b) an enzyme that converts acetoacetyl-CoA to 3-hydroxybutyryl-CoA, and (c) an enzyme that converts 3-hydroxybutyryl-CoA to polyhydroxybutyrate, and methods related thereto.

17 Claims, 7 Drawing Sheets

Specification includes a Sequence Listing.

WOOD-LJUNGDAHL MICROORGANISMS THAT PRODUCE POLYHYDROXYBUTYRATE

CROSS REFERENCE TO RELATED APPLICATIONS

This application claims the benefit of U.S. Patent Application 62/568,127 filed Oct. 4, 2017, the entirety of which is incorporated herein by reference.

FIELD OF THE INVENTION

The present invention relates to genetically engineered microorganisms and methods for the production of polyhydroxybutyrate (PHB) by microbial fermentation, particularly by microbial fermentation of a gaseous substrate.

BACKGROUND OF THE INVENTION

Petroleum-derived plastics have become essential to modern life, largely due to their lightness, robustness, durability, and resistance to degradation. However, dependence on petroleum-derived plastics has resulted in a score of serious problems, including crude oil depletion, pollution, and landfill accumulation. To decrease the environmental impacts of plastics, efforts are underway to replace conventional petroleum-derived polymers with biopolymers such as polylactide, polysaccharides, aliphatic polyesters and polyhydroxyalkanoates that possess similar physicochemical properties as conventional plastics (Anjum, *Int J Biol Macromol*, 89: 161-174, 2016). However, microorganisms and methods for producing such biopolymers are still largely undeveloped.

SUMMARY OF THE INVENTION

The invention provides a genetically engineered microorganism capable of producing PHB. In particular, the invention provides a non-naturally occurring Wood-Ljungdahl microorganism comprising (a) an enzyme that converts acetyl-CoA to acetoacetyl-CoA, (b) an enzyme that converts acetoacetyl-CoA to 3-hydroxybutyryl-CoA, and (c) an enzyme that converts 3-hydroxybutyryl-CoA to PHB.

In one embodiment, the enzyme that converts acetyl-CoA to acetoacetyl-CoA is an acetyl-CoA C-acetyltransferase (EC 2.3.1.9). For example, the acetyl-CoA C-acetyltransferase can be derived from *Acinetobacter baumannii, Aeromonas hydrophilia, Alcaligenes latus, Arthrospira platensis, Bacillus subtilis, Burkholderia cepacia, Clostridium acetobutylicum, Cupriavidus necator, Escherichia coli, Haloferax mediterranei, Pseudomonas aeruginosa, Pseudomonas fluorescens, Pseudomonas mandelii, Pseudomonas oleovorans, Pseudomonas putida*, or *Streptomyces coelicolor*.

In one embodiment, the enzyme that converts acetoacetyl-CoA to 3-hydroxybutyryl-CoA is an acetoacetyl-CoA reductase (EC 1.1.1.36) or a 3-hydroxybutyryl-CoA dehydrogenase (EC 1.1.1.157). For example, the acetoacetyl-CoA reductase can be derived from *Acinetobacter baumannii, Aeromonas hydrophilia, Alcaligenes latus, Arthrospira platensis, Bacillus subtilis, Burkholderia cepacia, Cupriavidus necator, Haloferax mediterranei, Pseudomonas aeruginosa, Pseudomonas fluorescens, Pseudomonas mandelii, Pseudomonas oleovorans, Pseudomonas putida*, or *Streptomyces coelicolor*. In another example, the 3-hydroxybutyryl-CoA dehydrogenase can be derived from *Clostridium beijerinckii, Clostridium acetobutylicum*, or *Clostridium kluyveri*.

In one embodiment, the enzyme that converts 3-hydroxybutyryl-CoA to polyhydroxybutyrate is a polyhydroxyalkanoate synthase (EC 2.3.1.-). For example, the polyhydroxyalkanoate synthase can be derived from *Acinetobacter baumannii, Aeromonas caviae, Aeromonas hydrophilia, Alcaligenes latus, Arthrospira platensis, Bacillus subtilis, Burkholderia cepacia, Cupriavidus necator, Haloferax mediterranei, Pseudomonas aeruginosa, Pseudomonas fluorescens, Pseudomonas mandelii, Pseudomonas oleovorans, Pseudomonas putida, Pseudomonas* sp. 61-3, *Rhodospirillum rubrum*, or *Streptomyces coelicolor*.

In one embodiment, the microorganism is a member of a genus selected from the group consisting of *Acetobacterium, Alkalibaculum, Blautia, Butyribacterium, Clostridium, Eubacterium, Moorella, Oxobacter, Sporomusa*, and *Thermoanaerobacter*. For example, the microorganism can be derived from a parental microorganism selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides*, and *Thermoanaerobacter kiuvi*. In a preferred embodiment, the microorganism is derived from a parental bacterium selected from the group consisting of *Clostridium autoethanogenum, Clostridium coskatii, Clostridium ljungdahlii*, and *Clostridium ragsdalei*.

In one embodiment, the microorganism consumes gaseous substrates comprising one or more of CO, $CO_2$, and $H_2$. In another embodiment, the microorganism is anaerobic. In yet another embodiment, the microorganism is not capable of degrading PHB.

The invention further provides a method of producing PHB comprising culturing the microorganism of the invention in the presence of a gaseous substrate. For example, the gaseous substrate can comprise one or more of CO, $CO_2$, and $H_2$. In one embodiment, the culturing is performed under anaerobic conditions. In another embodiment, the culturing is performed in the absence of carbohydrate substrates. In yet another embodiment, the culturing is performed in the absence of light.

These and other features and advantages of the present invention will be more fully understood from the following detailed description taken together with the accompanying claims. It is noted that the scope of the claims is defined by the recitations therein and not by the specific discussion of features and advantages set forth in the present description.

DESCRIPTION OF THE DRAWINGS

FIG. 4A (condition 1) shows a repeat of conditions used to generate the data observed in FIG. 3, using a gas mix comprising 50/18/3/29 of $CO/CO_2/H_2/N_2$ as the sole carbon source. FIG. 4B (condition 2) shows identical conditions as in condition 1 but with a new gas substrate (50/30/10/10 $CO/CO_2/H_2/N_2$). FIG. 4C (condition 3) shows identical conditions as in condition 2 but with an extended incubation time. FIG. 4D (condition 4) shows identical conditions as condition 3 but with periodical refreshing of the gas substrate. Values represent averages of biological triplicates plus or minus the standard deviations about those averages.

DESCRIPTION OF THE INVENTION

It has long been recognized that catalytic processes, such as the Fischer-Tropsch process, may be used to convert gases comprising carbon dioxide ($CO_2$), carbon monoxide (CO), and/or hydrogen ($H_2$), such as industrial waste gas or syngas, into a variety of fuels and chemicals. Recently, however, gas fermentation has emerged as an alternative platform for the biological fixation of such gases. In particular, acetogenic (i.e., Wood-Ljungdahl) microorganisms have been demonstrated to convert gases comprising CO, $CO_2$, and/or $H_2$ into products such as ethanol and 2,3-butanediol. The desirability of producing more complex polymer molecules, such as PHB, from these gases is well-documented (Drzyzga, *J Chem Technol Biotechnol*, 90: 1735-1751, 2015). However, the Wood-Ljungdahl pathway operates at the thermodynamic edge of life (Schuchmann, *Nat Rev Microbiol*, 12: 809-821, 2014), which makes it difficult for Wood-Ljungdahl microorganisms to accumulate even enough carbon for cell growth and maintenance, much less produce complex carbon products. These metabolic challenges are compounded by poor dissolution of gaseous substrates (e.g., CO, $CO_2$, and/or $H_2$) in fermentation media compared to carbohydrate or sugar substrates. Therefore, it would appear unlikely that Wood-Ljungdahl microorganisms could be engineered to synthesize PHB or other polyhydroxyalkanoates, especially since these polymers are natively produced by species such as *Rhodospirillum rubrum* and *Cupriavidus necator* as a means to store excess carbon. Indeed, to date, attempts to engineer acetogenic microorganisms to produce PHB from CO, $CO_2$, and/or $H_2$ have been unsuccessful (The European SYNPOL Project, Biopolymers from syngas fermentation, 2012-2017).

After diligent research and engineering efforts, however, the inventors have achieved the first-ever synthesis of PHB in Wood-Ljungdahl microorganisms. This represents a major milestone on the path to the production renewable and sustainable biopolymers.

In a first aspect, the invention provides a Wood-Ljungdahl microorganism capable of producing PHB. In a second aspect, the invention provides a method of producing PHB by culturing the aforementioned Wood-Ljungdahl microorganism in the presence of a gaseous substrate.

Pathway

Figure 1:
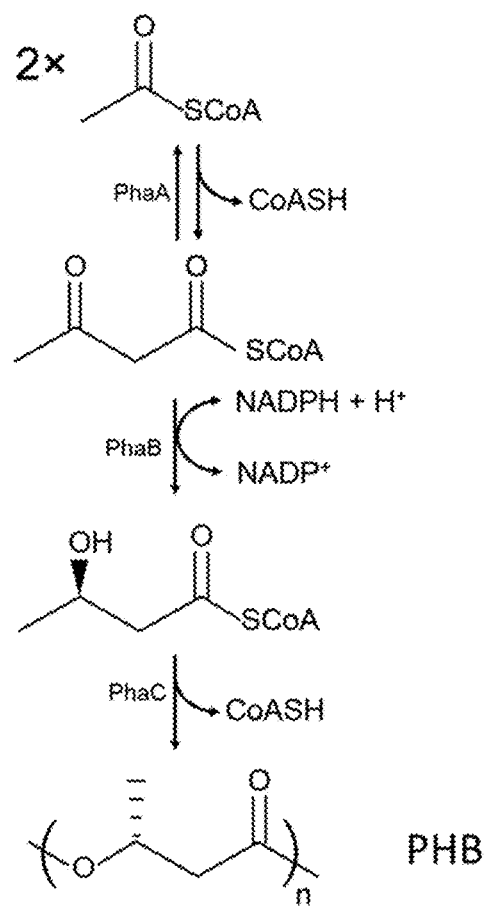
FIG. 1 is a diagram showing an enzymatic pathway to polyhydroxybutyrate (PHB) production.

Since Wood-Ljungdahl microorganisms do not natively produce PHB, the production of PHB in a Wood-Ljungdahl microorganism requires the introduction of at least one heterologous enzyme. The microorganism of the invention generally comprises three heterologous enzymes, namely (a) an enzyme that converts acetyl-CoA to acetoacetyl-CoA, (b) an enzyme that converts acetoacetyl-CoA to 3-hydroxybutyryl-CoA, and (c) an enzyme that converts 3-hydroxybutyryl-CoA to polyhydroxybutyrate. This pathway is depicted in FIG. 1.

(1) Conversion of Acetyl-CoA to Acetoacetyl-CoA

The conversion of acetyl-CoA to acetoacetyl-CoA may be catalyzed by any suitable enzyme. Although it is possible that native activity for this reaction may be present in certain acetogenic bacteria, it is usually necessary to introduce a heterologous (i.e., non-native) enzyme to catalyze this reaction. In a preferred embodiment, the enzyme is acetyl-CoA C-acetyltransferase (also known as thiolase or 3-ketothiolase), which has activity defined by EC 2.3.1.9 (i.e., 2 acetyl-CoA↔CoA+acetoacetyl-CoA). The acetyl-CoA C-acetyltransferase may be derived from any suitable host microorganism, such as *Acinetobacter baumannii, Aeromonas hydrophilia, Alcaligenes latus, Arthrospira platensis, Bacillus subtilis, Burkholderia cepacia, Clostridium acetobutylicum, Cupriavidus necator, Escherichia coli, Haloferax mediterranei, Pseudomonas aeruginosa, Pseudomonas fluo-*

*rescens, Pseudomonas mandelii, Pseudomonas oleovorans, Pseudomonas putida,* or *Streptomyces coelicolor.*

In particular, the acetyl-CoA C-acetyltransferase may be or may be derived from *Acinetobacter baumannii* PhaA (SCZ16966), *Aeromonas hydrophilia* PhaA (WP_043162470), *Alcaligenes latus* PhaA (AAC83659), *Arthrospira platensis* PhaA (WP_006617472), *Bacillus subtilis* PhaA (CUB52080), *Burkholderia cepacia* PhaA (WP_043187452), *Clostridium acetobutylicum* Th1A (WP_0109661571), *Cupriavidus necator* PhaA (WP_013956452.1), *Cupriavidus necator* BktB (WP_011615089.1), *Cupriavidus necator* phaA (WP_010810132.1), *Escherichia coli* AtoB (NP 416728.1), *Haloferax mediterranei* PhaA (WP_004059344), *Pseudomonas aeruginosa* PhaA (WP_038823536), *Pseudomonas fluorescens* PhaA (WP_073525707), *Pseudomonas mandelii* PhaA (WP_019582144), *Pseudomonas oleovorans* PhaA (WP_074859314), *Pseudomonas putida* PhaA (WP_058540218), or *Streptomyces coelicolor* PhaA (WP_011030221).

(2) Conversion of Acetoacetyl-CoA to 3-hydroxybutyryl-CoA

The conversion of acetoacetyl-CoA to 3-hydroxybutyryl-CoA may be catalyzed by any suitable enzyme. Although it is possible that native activity for this reaction may be present in certain acetogenic bacteria, it is usually necessary to introduce a heterologous (i.e., non-native) enzyme to catalyze this reaction. In a preferred embodiment, the enzyme is acetoacetyl-CoA reductase, which has activity defined by EC 1.1.1.36 (i.e., (R)-3-hydroxyacyl-CoA+NADP+$\leftrightarrow$3-oxoacyl-CoA+NADPH+H$^+$). The acetoacetyl-CoA reductase may be derived from any suitable host microorganism, such as *Acinetobacter baumannii, Aeromonas hydrophilia, Alcaligenes latus, Arthrospira platensis, Bacillus subtilis, Burkholderia cepacia, Cupriavidus necator, Haloferax mediterranei, Pseudomonas aeruginosa, Pseudomonas fluorescens, Pseudomonas mandelii, Pseudomonas oleovorans, Pseudomonas putida,* or *Streptomyces coelicolor.* In particular, the acetoacetyl-CoA reductase may be *Acinetobacter baumannii* PhaB (WP_095389464), *Aeromonas hydrophilia* PhaB (WP_041216919), *Alcaligenes latus* PhaB (AAC83660), *Arthrospira platensis* PhaB (WP_043469113), *Bacillus subtilis* PhaB (WP_070548955), *Burkholderia cepacia* PhaB (WP_059234032), *Cupriavidus necator* PhaB (WP_010810131.1), *Haloferax mediterranei* PhaB (WP_004572392), *Pseudomonas aeruginosa* PhaB (WP_031690879), *Pseudomonas fluorescens* PhaB (WP_030141425), *Pseudomonas mandelii* PhaB (WP_094467462), *Pseudomonas oleovorans* PhaB (WP_074858624), *Pseudomonas putida* PhaB (BAB96554), or *Streptomyces coelicolor* PhaB (WP_011027734). In another preferred embodiment, the enzyme is 3-hydroxybutyryl-CoA dehydrogenase, which has activity defined by EC 1.1.1.157 (i.e., (S)-3-hydroxybutanoyl-CoA+NADP$^+$=3-acetoacetyl-CoA+NADPH+H$^+$). The 3-hydroxybutyryl-CoA dehydrogenase may be or may be derived from derived from any suitable host microorganism, such as *Clostridium beijerinckii, Clostridium acetobutylicum,* or *Clostridium kluyveri.* In particular, the 3-hydroxybutyryl-CoA dehydrogenase may be *Clostridium beijerinckii* Hbd (WP_011967675.1), *Clostridium acetobutylicum* Hbd (NP_349314.1), or *Clostridium kluyveri* Hbd1 (WP_011989027.1).

Preferably, the enzyme that converts acetoacetyl-CoA to 3-hydroxybutyryl-CoA is (R)-specific, i.e., produces (R)-3-hydroxybutyryl-CoA, since (R)-3-hydroxybutyryl-CoA is the typical substrate for the enzymatic production of PHB. However, in some instances, the enzyme that converts acetoacetyl-CoA to 3-hydroxybutyryl-CoA is (S)-specific, i.e., produces (S)-3-hydroxybutyryl-CoA. Without wishing to be bound by any particular theory, the inventors believe that native or introduced epimerase activity in acetogenic bacteria may allow for the interconversion of (S)- and (R)-3-hydroxybutyryl-CoA, such (S)-3-hydroxybutyryl-CoA may be converted to (R)-3-hydroxybutyryl-CoA, which may then be converted to PHB.

(3) Conversion of 3-hydroxybutyryl-CoA to PHB

The conversion of 3-hydroxybutyryl-CoA to PHB may be catalyzed by any suitable enzyme. Although it is possible that native activity for this reaction may be present in certain acetogenic bacteria, it is usually necessary to introduce a heterologous (i.e., non-native) enzyme to catalyze this reaction. In a preferred embodiment, the enzyme is polyhydroxyalkanoate synthase, which has activity defined by EC 2.3.1.-, such as EC 2.3.1.B2 (type I) (i.e., 3-hydroxybutyryl-CoA+[(R)-3-hydroxybutanoate]$_n$=[(R)-3-hydroxybutanoate]$_{n+1}$+CoA), EC 2.3.1.B3 (type II) (i.e., 3-hydroxyacyl-CoA+[(R)-3-hydroxyacyl]$_n$=[(R)-3-hydroxyacyl]$_{n+1}$+CoA), or EC 2.3.1.B4 (type III) (i.e., 3-hydroxyacyl-CoA+[(R)-3-hydroxyacyl]$_n$=[(R)-3-hydroxyacyl]$_{n+1}$+CoA). This enzyme may also be referred to as polyhydroxyalkanoate polymerase, polyhydroxybutyrate synthase, polyhydroxybutyrate polymerase, and the like. The polyhydroxyalkanoate synthase may be derived from any suitable host microorganism, such as *Acinetobacter baumannii, Aeromonas caviae, Aeromonas hydrophilia, Alcaligenes latus, Arthrospira platensis, Bacillus subtilis, Burkholderia cepacia, Cupriavidus necator, Haloferax mediterranei, Pseudomonas aeruginosa, Pseudomonas fluorescens, Pseudomonas mandelii, Pseudomonas oleovorans, Pseudomonas putida, Pseudomonas* sp. 61-3, *Rhodospirillum rubrum,* or *Streptomyces coelicolor.* In particular, the polyhydroxyalkanoate synthase may be or may be derived from *Acinetobacter baumannii* PhaC (SCY71072), *Aeromonas caviae* PhaC (WP_045524574), *Aeromonas hydrophilia* PhaC1 (WP_017780191) or PhaC2 (AAV41872), *Alcaligenes latus* PhaC (WP_084267317), *Arthrospira platensis* PhaC (WP_006617456), *Bacillus subtilis* PhaC (CUB58881), *Burkholderia cepacia* PhaC (WP_027784567), *Cupriavidus necator* PhaC (WP_011615085 or WP_013956451.1), *Haloferax mediterranei* PhaC (WP_004056138), *Pseudomonas aeruginosa* PhaC1 (WP_038823539) or PhaC2 (WP_025271419), *Pseudomonas fluorescens* PhaC1 (WP_057399292) or PhaC2 (WP_030141001), *Pseudomonas mandelii* PhaC1 (WP_094467460) or PhaC2 (WP_010465951), *Pseudomonas oleovorans* PhaC1 (AAL17611) or PhaC2 (WP_037049875), *Pseudomonas putida* PhaC1 (BAB96552) or PhaC2 (WP_029886362), *Pseudomonas* sp. 61-3 PhaC1 (BAA36198) or PhaC2 (BAA36202), *Rhodospirillum rubrum* PhaC1 (WP_011388028), PhaC2 (WP_011390166), or PhaC3 (WP_011398569), or *Streptomyces coelicolor* PhaC.

In certain embodiments, one or more disruptive mutations may be introduced to one or more endogenous enzymes to reduce or eliminate competition with introduced heterologous enzymes. In particular, a "disruptive mutation" is a mutation that reduces or eliminates (i.e., "disrupts") the expression or activity of a gene or enzyme. The disruptive mutation may partially inactivate, fully inactivate, or delete the gene or enzyme. The disruptive mutation may be a knockout (KO) mutation. The disruptive mutation may be any mutation that reduces, prevents, or blocks the biosynthesis of a product produced by an enzyme. The disruptive mutation may include, for example, a mutation in a gene encoding an enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, siRNA, guide RNA) and/or protein (e.g., a Cas protein) which inhibits the expression of an enzyme. The disruptive mutation may be introduced using any method known in the art.

For example, the microorganism of the invention may have a disruptive mutation in an endogenous thioesterase enzyme. Three putative thioesterases have been identified in *Clostridium autoethanogenum*: (1) "thioesterase 1" (AGY74947.1; annotated as palmitoyl-CoA hydrolase), (2) "thioesterase 2" (AGY75747.1; annotated as 4-hydroxybenzoyl-CoA thioesterase), and (3) "thioesterase 3" (AGY75999.1; annotated as putative thioesterase). Three putative thioesterases have also been identified in *Clostridium ljungdahlii*: (1) "thioesterase 1" (ADK15695.1; annotated as predicted acyl-CoA thioesterase 1), (2) "thioesterase 2" (ADK16655.1; annotated as predicted thioesterase), and (3) "thioesterase 3" (ADK16959.1; annotated as predicted thioesterase). The disruptive mutation may affect any of these thioesterases or any other thioesterases that may be endogenous to the microorganism of the invention.

Microorganism

A "microorganism" is a microscopic organism, especially a bacterium, archea, virus, or fungus. The microorganism of the invention is typically a bacterium. As used herein, recitation of "microorganism" should be taken to encompass "bacterium."

The microorganism of the invention is non-naturally occurring. The term "non-naturally occurring" when used in reference to a microorganism is intended to mean that the microorganism has at least one genetic modification not found in a naturally occurring strain of the referenced species, including wild-type strains of the referenced species. Non-naturally occurring microorganisms are typically developed in a laboratory or research facility. In contrast, "wild-type" refers to the typical form of an organism, strain, gene, or characteristic as it occurs in nature.

The terms "genetic modification," "genetic alteration," or "genetic engineering" broadly refer to manipulation of the genome or nucleic acids of a microorganism by the hand of man. Likewise, the terms "genetically modified," "genetically altered," or "genetically engineered" refer to a microorganism comprising such a genetic modification, genetic alteration, or genetic engineering. These terms may be used to differentiate a laboratory-generated microorganism from a naturally-occurring microorganism. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization.

"Recombinant" indicates that a nucleic acid, protein, or microorganism is the product of genetic modification, engineering, or recombination. Generally, the term "recombinant" refers to a nucleic acid, protein, or microorganism that comprises or is encoded by genetic material derived from multiple sources, such as two or more different strains or species of microorganisms. The microorganism of the invention is typically recombinant.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the invention is derived from a "parental microorganism," which is a microorganism used to generate a microorganism of the invention. The parental microorganism may be a naturally-occurring microorganism (i.e., a wild-type microorganism) or a microorganism that has been previously modified (i.e., a mutant or recombinant microorganism). The microorganism of the invention may be modified to express or overexpress one or more enzymes that were not expressed or overexpressed in the parental microorganism. Similarly, the microorganism of the invention may be modified to comprise one or more genes that were not comprised by the parental microorganism. The microorganism of the invention may also be modified to not express or to express lower amounts of one or more enzymes that were expressed in the parental microorganism. In one embodiment, the microorganism of the invention is derived from a parental microorganism selected from the group consisting of *Clostridium autoethanogenum*, *Clostridium ljungdahlii*, or *Clostridium ragsdalei*. In a preferred embodiment, the microorganism of the invention is derived from the parental microorganism *Clostridium autoethanogenum* LZ1561, which was deposited on Jun. 7, 2010 with Deutsche Sammlung von Mikroorganismen und Zellkulturen GmbH (DSMZ) located at Inhoffenstraβ 7B, D-38124 Braunschwieg, Germany on Jun. 7, 2010 under the terms of the Budapest Treaty and accorded accession number DSM23693. This strain is described in International Patent Application No. PCT/NZ2011/000144, which published as WO 2012/015317.

The microorganism of the invention may be further classified based on functional characteristics. For example, the microorganism of the invention may be or may be derived from a Wood-Ljungdahl microorganism, a C1-fixing microorganism, an anaerobe, an acetogen, an ethanologen, and/or a carboxydotroph. Table 1 provides a representative list of microorganisms and identifies their functional characteristics.

TABLE 1

|  | Wood-Ljungdahl | C1-fixing | Anaerobe | Acetogen | Ethanologen | Autotroph | Carboxydotroph |
|---|---|---|---|---|---|---|---|
| *Acetobacterium woodii* | + | + | + | + | +/−[1] | + | − |
| *Alkalibaculum bacchii* | + | + | + | + | + | + | + |
| *Blautia producta* | + | + | + | + | − | + | + |
| *Butyribacterium methylotrophicum* | + | + | + | + | + | + | + |
| *Clostridium aceticum* | + | + | + | + | − | + | + |
| *Clostridium autoethanogenum* | + | + | + | + | + | + | + |
| *Clostridium carboxidivorans* | + | + | + | + | + | + | + |

TABLE 1-continued

| | Wood-Ljungdahl | C1-fixing | Anaerobe | Acetogen | Ethanologen | Autotroph | Carboxydotroph |
|---|---|---|---|---|---|---|---|
| Clostridium coskatii | + | + | + | + | + | + | + |
| Clostridium drakei | + | + | + | + | − | + | + |
| Clostridium formicoaceticum | + | + | + | + | − | + | + |
| Clostridium ljungdahlii | + | + | + | + | + | + | + |
| Clostridium magnum | + | + | + | + | − | + | +/− [2] |
| Clostridium ragsdalei | + | + | + | + | + | + | + |
| Clostridium scatologenes | + | + | + | + | − | + | + |
| Eubacterium limosum | + | + | + | + | − | + | + |
| Moorella thermautotrophica | + | + | + | + | + | + | + |
| Moorella thermoacetica (formerly Clostridium thermoaceticum) | + | + | + | + | − [3] | + | + |
| Oxobacter pfennigii | + | + | + | + | − | + | + |
| Sporomusa ovata | + | + | + | + | − | + | +/− [4] |
| Sporomusa silvacetica | + | + | + | + | − | + | +/− [5] |
| Sporomusa sphaeroides | + | + | + | + | − | + | +/− [6] |
| Thermoanaerobacter kiuvi | + | + | + | + | − | + | − |

[1] *Acetobacterium woodi* can produce ethanol from fructose, but not from gas.
[2] It has not been investigated whether *Clostridium magnum* can grow on CO.
[3] One strain of *Moorella thermoacetica*, *Moorella* sp. HUC22-1, has been reported to produce ethanol from gas.
[4] It has not been investigated whether *Sporomusa ovata* can grow on CO.
[5] It has not been investigated whether *Sporomusa silvacetica* can grow on CO.
[6] It has not been investigated whether *Sporomusa sphaeroides* can grow on CO.

"Wood-Ljungdahl" refers to the Wood-Ljungdahl pathway of carbon fixation as described, e.g., by Ragsdale, Biochim Biophys Acta, 1784: 1873-1898, 2008. "Wood-Ljungdahl microorganisms" refers, predictably, to microorganisms comprising the Wood-Ljungdahl pathway. Generally, the microorganism of the invention comprises a native Wood-Ljungdahl pathway. Herein, a Wood-Ljungdahl pathway may be a native, unmodified Wood-Ljungdahl pathway or it may be a Wood-Ljungdahl pathway with some degree of genetic modification (e.g., overexpression, heterologous expression, knockout, etc.) so long as it still functions to convert CO, $CO_2$, and/or $H_2$ to acetyl-CoA.

"C1" refers to a one-carbon molecule, for example, CO, $CO_2$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism of the invention is a C1-fixing bacterium. In a preferred embodiment, the microorganism of the invention is derived from a C1-fixing microorganism identified in Table 1. For the purposes of the present invention, methane ($CH_4$) could be considered a C1-carbon source, but only if the bacterium of the invention was engineered to comprise a methane metabolic pathway, as described, e.g., in WO 2016/138050, since acetogenic bacteria are not natively capable of using methane as a carbon source.

An "anaerobe" is a microorganism that does not require oxygen for growth. An anaerobe may react negatively or even die if oxygen is present above a certain threshold. However, some anaerobes are capable of tolerating low levels of oxygen (e.g., 0.000001-5% oxygen). Typically, the microorganism of the invention is an anaerobe. In a preferred embodiment, the microorganism of the invention is derived from an anaerobe identified in Table 1.

"Acetogens" are obligately anaerobic bacteria that use the Wood-Ljungdahl pathway as their main mechanism for energy conservation and for synthesis of acetyl-CoA and acetyl-CoA-derived products, such as acetate (Ragsdale, Biochim Biophys Acta, 1784: 1873-1898, 2008). Acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York, N.Y., 2006). All naturally occurring acetogens are C1-fixing, anaerobic, autotrophic, and non-methanotrophic. Typically, the microorganism of the invention is an acetogen. In a preferred embodiment, the microorganism of the invention is derived from an acetogen identified in Table 1.

An "ethanologen" is a microorganism that produces or is capable of producing ethanol. Typically, the microorganism of the invention is an ethanologen. In a preferred embodiment, the microorganism of the invention is derived from an ethanologen identified in Table 1.

An "autotroph" is a microorganism capable of growing in the absence of organic carbon. Instead, autotrophs use inorganic carbon sources, such as CO and/or $CO_2$. Typically, the microorganism of the invention is an autotroph. In a preferred embodiment, the microorganism of the invention is derived from an autotroph identified in Table 1.

A "carboxydotroph" is a microorganism capable of utilizing CO as a sole source of carbon and energy. Typically, the microorganism of the invention is a carboxydotroph. In a preferred embodiment, the microorganism of the invention is derived from a carboxydotroph identified in Table 1.

More broadly, the microorganism of the invention may be derived from any genus or species identified in Table 1. For example, the microorganism may be a member of a genus selected from the group consisting of *Acetobacterium, Alkalibaculum, Blautia, Butyribacterium, Clostridium, Eubacterium, Moorella, Oxobacter, Sporomusa,* and *Thermoanaerobacter*. In particular, the microorganism may be derived from a parental bacterium selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei,*

*Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides,* and *Thermoanaerobacter kiuvi.*

In a preferred embodiment, the microorganism of the invention is derived from the cluster of Clostridia comprising the species *Clostridium autoethanogenum, Clostridium coskatii, Clostridium ljungdahlii,* and *Clostridium ragsdalei.* These species were first reported and characterized by Abrini, *Arch Microbiol,* 161: 345-351, 1994 (*Clostridium autoethanogenum*), Tanner, *Int J System Bacteriol,* 43: 232-236, 1993 (*Clostridium ljungdahlii*), and Huhnke, WO 2008/028055 (*Clostridium ragsdalei*).

These species have many similarities. In particular, these species are all C1-fixing, anaerobic, acetogenic, ethanologenic, and carboxydotrophic members of the genus *Clostridium.* These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 pin), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, *Biotechnol Bioeng,* 110:1066-1077, 2012). Importantly, these species also all show strong autotrophic growth on CO-comprising gases, produce ethanol and acetate (or acetic acid) as main fermentation products, and produce small amounts of 2,3-butanediol and lactic acid under certain conditions.

However, these species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Kopke, *Curr Opin Biotechnol,* 22: 320-325, 2011).

Thus, in summary, many of the characteristics of *Clostridium autoethanogenum, Clostridium coskatii, Clostridium ljungdahlii,* or *Clostridium ragsdalei* are not specific to that species, but are rather general characteristics for this cluster of C1-fixing, anaerobic, acetogenic, ethanologenic, and carboxydotrophic members of the genus *Clostridium.* However, since these species are, in fact, distinct, the genetic modification or manipulation of one of these species may not have an identical effect in another of these species. For instance, differences in growth, performance, or product production may be observed.

The microorganism of the invention may also be derived from an isolate or mutant of *Clostridium autoethanogenum, Clostridium coskatii, Clostridium ljungdahlii,* or *Clostridium* ragsdalei. Isolates and mutants of *Clostridium autoethanogenum* include JA1-1 (DSM10061) (Abrini, *Arch Microbiol,* 161: 345-351, 1994), LBS1560 (DSM19630) (WO 2009/064200), and LZ1561 (DSM23693) (WO 2012/015317). Isolates and mutants of *Clostridium ljungdahlii* include ATCC 49587 (Tanner, *Int J Syst Bacteriol,* 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), O-52 (ATCC 55989) (U.S. Pat. No. 6,368,819), and OTA-1 (Tirado-Acevedo, Production of bioethanol from synthesis gas using *Clostridium ljungdahlii,* PhD thesis, North Carolina State University, 2010). Isolates and mutants of *Clostridium ragsdalei* include PI 1 (ATCC BAA-622, ATCC PTA-7826) (WO 2008/028055).

Preferably, the microorganism of the invention is not phototrophic or photosynthetic. Preferably, the microorganism of the invention is not methanotrophic.

Preferably, the microorganism of the invention is not a member of the genus *Alcaligenes, Azotobacter, Bacillus, Cupriavidus* (*Ralstonia*), *Rhizobium, Rhodospirillum,* or *Pseudomonas.* In particular, the microorganism of the invention is preferably not derived from *Rhodospirillum rubrum, Bacillus cereus, Cupriavidus* necator (formerly *Ralstonia eutropha*), or *Pseudomonas putida.* In other embodiments, the microorganism of the invention is preferably not derived from *Escherichia coli.*

Enzymes

"Endogenous" or "native" refers to a nucleic acid or protein that is present or expressed in the wild-type or parental microorganism from which the microorganism of the invention is derived. For example, an endogenous gene or protein is a gene or protein that is natively present in the wild-type or parental microorganism from which the microorganism of the invention is derived. In one embodiment, the expression of an endogenous gene may be controlled by an exogenous regulatory element, such as an exogenous promoter.

"Exogenous" refers to a nucleic acid or protein that originates outside the microorganism of the invention. For example, an exogenous gene or enzyme may be artificially or recombinantly created and introduced to or expressed in the microorganism of the invention. An exogenous gene or enzyme may also be isolated from a heterologous microorganism and introduced to or expressed in the microorganism of the invention. Exogenous nucleic acids may be adapted to integrate into the genome of the microorganism of the invention or to remain in an extra-chromosomal state in the microorganism of the invention, for example, in a plasmid.

"Heterologous" refers to a nucleic acid or protein that is not present in the wild-type or parental microorganism from which the microorganism of the invention is derived. For example, a heterologous gene or enzyme may be derived from a different strain or species and introduced to or expressed in the microorganism of the invention.

Typically, at least one of the enzymes that (a) converts acetyl-CoA to acetoacetyl-CoA, (b) converts acetoacetyl-CoA to 3-hydroxybutyryl-CoA, or (c) converts 3-hydroxybutyryl-CoA to PHB is heterologous (i.e., non-native) to the bacterium. For example, one, two, or all three of these enzymes may be heterologous (i.e., non-native) to the bacterium. If the bacterium happens to have native enzymatic activity for one or more of these steps, however, it may not be necessary to introduce heterologous enzymes to catalyze those steps.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins.

"Enzyme activity," or simply "activity," refers broadly to enzymatic activity, including, but not limited, to the activity of an enzyme, the amount of an enzyme, or the availability of an enzyme to catalyze a reaction. Accordingly, "increasing" enzyme activity includes increasing the activity of an enzyme, increasing the amount of an enzyme, or increasing the availability of an enzyme to catalyze a reaction. Similarly, "decreasing" enzyme activity includes decreasing the activity of an enzyme, decreasing the amount of an enzyme, or decreasing the availability of an enzyme to catalyze a reaction.

"Codon optimization" refers to the mutation of a nucleic acid, such as a gene, for optimized or improved translation of the nucleic acid in a particular strain or species. Codon optimization may result in faster translation rates or higher translation accuracy. In a preferred embodiment, the genes of the invention are codon optimized for expression in *Clostridium*, particularly *Clostridium autoethanogenum, Clostridium coskatii, Clostridium ljungdahlii*, or *Clostridium ragsdalei*. As used herein, the terms "codon-optimized" and "codon-adapted" can be used interchangeably.

The term "variants" includes nucleic acids and proteins whose sequence varies from the sequence of a reference nucleic acid and protein, such as a sequence of a reference nucleic acid and protein disclosed in the prior art or exemplified herein. The invention may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

Such nucleic acids or proteins may be referred to herein as "functionally equivalent variants." By way of example, functionally equivalent variants of a nucleic acid may include allelic variants, fragments of a gene, mutated genes, polymorphisms, and the like. Homologous genes from other microorganisms are also examples of functionally equivalent variants. These may include homologous genes in species such as *Clostridium acetobutylicum, Clostridium beijerinckii*, or *Clostridium ljungdahlii*, the details of which are publicly available on websites such as GenBank or NCBI. Functionally equivalent variants also include nucleic acids whose sequence varies as a result of codon optimization for a particular microorganism. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant of a protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art.

The enzymes described herein are typically expressed from a nucleic acid that has been introduced into the microorganism of the invention. Nucleic acids may be delivered to a microorganism of the invention using any method known in the art. For example, nucleic acids may be delivered as naked nucleic acids or may be formulated with one or more agents, such as liposomes. The nucleic acids may be DNA, RNA, cDNA, or combinations thereof, as is appropriate. Restriction inhibitors may be used in certain embodiments. Additional vectors may include plasmids, viruses, bacteriophages, cosmids, and artificial chromosomes. In a preferred embodiment, nucleic acids are delivered to the microorganism of the invention using a plasmid. By way of example, transformation (including transduction or transfection) may be achieved by electroporation, ultra-sonication, polyethylene glycol-mediated transformation, chemical or natural competence, protoplast transformation, prophage induction, or conjugation. In certain embodiments having active restriction enzyme systems, it may be necessary to methylate a nucleic acid before introduction of the nucleic acid into a microorganism.

Furthermore, nucleic acids may be designed to comprise a regulatory element, such as a promoter, to increase or otherwise control expression of a particular nucleic acid. The promoter may be a constitutive promoter or an inducible promoter. Ideally, the promoter is a Wood-Ljungdahl pathway promoter, a ferredoxin promoter, a pyruvate:ferredoxin oxidoreductase promoter, an Rnf complex operon promoter, an ATP synthase operon promoter, or a phosphotransacetylase/acetate kinase operon promoter.

Substrates

"Substrate" refers to a carbon and/or energy source for the microorganism of the invention. Typically, the substrate is gaseous and comprises a C1-carbon source, for example, CO and/or $CO_2$. Preferably, the substrate comprises a C1-carbon source of CO or CO+$CO_2$. The substrate may further comprise other non-carbon components, such as $H_2$, $N_2$, or electrons.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the invention typically converts at least a portion of the CO in the substrate to a product. In some embodiments, the substrate comprises no or substantially no (<1 mol %) CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no (<1 mol %) $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no (<1 mol %) $CO_2$.

In certain embodiments, growth of a PHB-producing strain is compared to a control ("empty plasmid" or "EP") strain using two different CO and $CO_2$ containing gas mixes with either 20% of $H_2$ resembling syngas (50% CO, 20% $CO_2$, 20% $H_2$, 10% Argon), termed as conditions "PHB20" and "EP20," respectively, or 2% of $H_2$ resembling steel mill off gas (50% CO, 20% $CO_2$, 2% $H_2$, 28% Nitrogen), termed as conditions "PHB2" and "EP2," respectively.

Although the substrate is typically gaseous, the substrate may also be provided in alternative forms. For example, the substrate may be dissolved in a liquid saturated with a CO-comprising gas using a microbubble dispersion generator. By way of further example, the substrate may be adsorbed onto a solid support.

The substrate and/or C1-carbon source may be a waste gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

In certain embodiments, the fermentation or culturing is performed in the absence of carbohydrate substrates, such as sugar, starch, lignin, cellulose, or hemicellulose.

As used herein, the term "PHBLowB" is used to refer to experiments with a lower steady-state biomass concentration, such as a 3-times lower steady-state biomass concentration. As used herein, the term "PHBpH5.5" is used to refer to experiments conducted at a pH of 5.5. See FIG. 8.

Products

The microorganism of the invention may be cultured to produce one or more products. In particular, the microorganism of the invention may produce PHB or precursors thereof, such as acetoacetyl-CoA or 3-hydroxybutyryl-CoA.

PHB is a polymer of 3-hydroxybutyrate monomers. The PHB produced according to the invention may comprise any number of 3-hydroxybutyrate monomers, for example, about 10-1,000,000 monomers. As further examples, the PHB may comprise about 10-100,000 monomers, 100-100,000 monomers, 100-10,000 monomers, 500-5,000 monomers, 1,000-10,000 monomers, or 5,000-20,000 monomers. In a preferred embodiment, the PHB comprises about 100-12,000 monomers.

The molecular weight of PHB produced by the bacterium of the invention may be in the range of about 1,000-100,000,000 Da. For instance, the molecular weight of the PHB may be about 1,000-10,000 Da, 10,000-1,000,000 Da, 10,000-10,000,000 Da, or 10,000,000-100,000,000 Da. Preferably, the molecular weight of the PHB may be about 10,000-1,000,000 Da, such as 10,000-100,000 Da, 10,000-500,000 Da, 100,000-500,000 Da, 300,000-800,000 Da, or 500,000-1,000,000 Da.

PHB production is frequently referred to as a percentage of dry cellular weight. The microorganism of the invention may produce, for example, 0.005-0.995 wt % PHB. Preferably, the microorganism of the invention produces about 0.01 wt %, 0.1 wt %, 0.5 wt %, 1 wt %, 1.5 wt %, 2 wt %, 3 wt %, 5 wt %, 10 wt %, 20 wt %, 30 wt %, 40 wt %, 50 wt %, 60 wt %, 70 wt %, 80 wt %, 90 wt %, or 95 wt % PHB.

The physical characteristics of PHB are well known in the art. As a rough approximation, PHB has a Young's modulus of 1497-3500 MPa, a tensile strength of 18-43 MPa, elongation to break of 1.9-45%, a crystallinity of 60-80%, a melting temperature of 162-180° C., a crystallization temperature of 45-116° C., and/or a glass-transition temperature of −1.2-10° C.

Additionally, the microorganism of the invention may also produce or may be engineered to produce other products, such as ethanol (WO 2007/117157), acetate (WO 2007/117157), butanol (WO 2008/115080 and WO 2012/053905), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), isoprene (WO 2013/180584), fatty acids (WO 2013/191567), 2-butanol (WO 2013/185123), 1,2-propanediol (WO 2014/036152), 1-propanol (WO 2014/0369152), and chorismate-derived products (WO 2016/191625). In addition to one or more target products, the microorganism of the invention may also produce ethanol, acetate, and/or 2,3-butanediol. In certain embodiments, microbial biomass itself may be considered a product.

Preferably, the microorganism of the invention is not capable of degrading PHB. Organisms that natively produce PHB and other polyhydroxyalkanoates generally synthesize the polymers as a carbon storage material when other nutrients (e.g., nitrogen and phosphorous) are limiting and carbon is in excess. These organisms can then depolymerize/degrade the polymers when the limiting nutrient is replenished to have access to the stored carbon. For the purposes of maximizing PHB production, non-native producers, such as the microorganisms of the present invention, often have the advantage of not being capable of enzymatically degrading the polymers once they are produced. This essentially locks the carbon into the polymers permanently and can increase the yield.

"Selectivity" refers to the ratio of the production of a target product to the production of all fermentation products produced by a microorganism. The microorganism of the invention may be engineered to produce products at a certain selectivity or at a minimum selectivity. In one embodiment, a target product accounts for at least about 5%, 10%, 15%, 20%, 30%, 50%, or 75% of all fermentation products produced by the microorganism of the invention. In one embodiment, the target product accounts for at least 10% of all fermentation products produced by the microorganism of the invention, such that the microorganism of the invention has a selectivity for the target product of at least 10%. In another embodiment, the target product accounts for at least 30% of all fermentation products produced by the microorganism of the invention, such that the microorganism of the invention has a selectivity for the target product of at least 30%.

Fermentation

The invention further provides a method of producing PHB comprising culturing the microorganism of the invention in the presence of a gaseous substrate, whereby the microorganism produces PHB. The gaseous substrate generally comprises one or more of CO, $CO_2$, and $H_2$.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that comprises nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture should desirably be carried out under appropriate conditions for production of the target product. Typically, the culture is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition.

Operating a bioreactor at elevated pressures allows for an increased rate of gas mass transfer from the gas phase to the liquid phase. Accordingly, it may be preferable to perform the fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time, in turn, dictates the required volume of a bioreactor, the use of pressurized systems can greatly reduce the volume of the bioreactor required, and consequently the capital cost of the fermentation equipment.

In certain embodiments, the fermentation is performed in the absence of light or in the presence of an amount of light insufficient to meet the energetic requirements of photosynthetic or phototrophic microorganisms.

The methods of the invention may further involve separation or purification of PHB. The PHB may be separated or purified using any method known in the art. For example, cells may be collected by precipitation (Chen, *Appl Microbiol Biotechnol*, 57: 50-55, 2001) or continuous separation (Elbahloul, *Appl Environ Microbiol*, 75: 643-651, 2009; Heinrich, *AMB Express*, 2: 59, 2012) followed by lyophilization. Subsequent to freeze-drying, the polymer may be removed from cells with materials such as ethyl acetate (Chen, *Appl Microbiol Biotechnol*, 57: 50-55, 2001), acetone (Elbahloul, *Appl Environ Microbiol*, 75: 643-651, 2009), or sodium hypochlorite (Heinrich, *AMB Express*, 2: 59, 2012). The polymer may then be removed from residual/solubilized cell mass. A great number of alternative processes for purification of polyhydroxyalkanoates have been published and been developed but have not yet been established for larger-scale purification (Kunasundari, *Express Polym Lett*, 5, 620-634, 2011).

EXAMPLES

The following examples further illustrate the invention but, of course, should not be construed to limit its scope in any way.

Example 1

This example demonstrates construction of a Wood-Ljungdahl microorganism capable of PHB synthesis.

Figure 2:
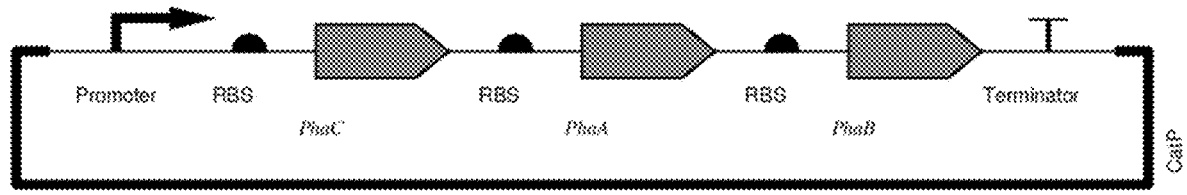
FIG. 2 is a plasmid map of pPHB_01.

PHB pathway genes (phaC, phaA, and phaB) from *C. necator* (SEQ ID NOs: 1, 4, and 7) were introduced into *C. autoethanogenum*, a Wood-Ljungdahl microorganism that does not natively produce PHB. Of note, these species have significant differences in chromosomal GC-content. Specifically, *C. necator* has 66% GC-content (Pohlmann, *Nat Biotechnol*, 24: 1257-1262, 2006) and *C. autoethanogenum* has only 31% GC-content (Brown, *Biotechnol Biofuels*, 7: 40, 2014). Anticipating gene expression issues based on codon usage, the sequences of the PHB genes from *C. necator* were codon-adapted to better fit a higher expression profile for proteins in *C. autoethanogenum*. The genes, with novel sequences (SEQ ID NOs: 3, 6, and 9) coding for identical proteins as in *C. necator*, were synthesized and assembled into the expression vector pMTL83157 (SEQ ID NO: 10). This plasmid is similar to the pMTL8000 series (Heap, *J Microbiol Methods*, 78: 79-85, 2009) with a native Wood-Ljungdahl promoter taken from *C. autoethanogenum* to drive gene transcription. The genes were placed downstream of the promoter in the same order as they appear in the *C. necator* genome: phaC, phaA, and phaB. An antibiotic selection marker, catP, was also used. The resulting plasmid was named pPHB_01 (SEQ ID NO: 11) (FIG. 2).

pPHB_01 was inserted into *C. autoethanogenum* by bacterial conjugation using *E. coli* HB101, as described elsewhere (Mock, *J Bacteriol*, 197: 2965-2980, 2015). Separately, an "empty" pMTL83157 plasmid was inserted into *C. autoethanogenum* to serve as a negative control. These strains were then used to test PHB production from gaseous substrates.

In a preferred embodiment, the microorganism comprises enzyme that converts aceyl-CoA to acetoacetyl-CoA comprises an enzyme having at least 80% sequence identity to the amino acid sequence set forth in SEQ ID NO: 2, the enzyme that converts acetoacetyl-CoA to 3-hydroxybutyryl-CoA comprises an enzyme having at least 80% sequence identity to the amino acid sequence set forth in SEQ ID NO: 5, and/or the enzyme that converts 3-hydroxybutyryl-CoA to polyhydroxybutyrate comprises an enzyme having at least 80% sequence identity to the amino acid sequence set forth in SEQ ID NO: 8.

Example 2

This example demonstrates the production of PHB from gaseous substrates in Schott bottles.

The strains constructed in Example 1 were grown in small batches to test for production of PHB. All work was conducted under strict anaerobic conditions (Hungate, Methods in microbiology, pages 117-132, Academic Press, New York, N.Y., 1969). Pressure-rated Schott bottles comprising modified PETC media (Kopke, *Appl Environ Microbiol*, 77: 5467-5475, 2011) with thiamphenicol for plasmid retention and 2-(N-morpholino) ethanesulfonic acid for buffering were inoculated with the strains, and gas comprising CO, $CO_2$, $H_2$, and $N_2$ (at 50, 18, 3, and 29%, respectively) as the sole carbon source was added to the bottles to 21 psi. The cultures were grown at 37° C. with rotary shaking.

Cell growth was monitored periodically until the cultures entered stationary phase. Upon completion of growth, the cells were no longer handled under anaerobic conditions. The cells were collected by centrifugation, their supernatants discarded, frozen at −20° C., and dried via lyophilization.

Figure 3:
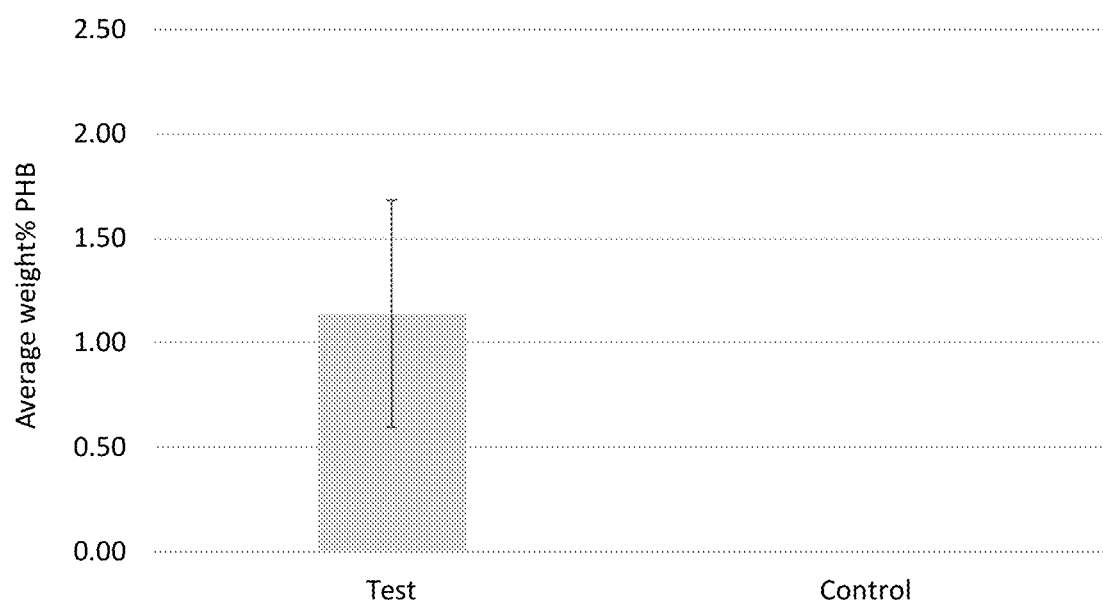
FIG. 3 is a graph showing PHB production in *C. autoethanogenum* carrying either a plasmid with a PHB biosynthesis pathway (pPHB_01) or an empty plasmid (pMTL83157) as a negative control. The bacteria were grown anaerobically in pressure-rated bottles with only CO and $CO_2$ as carbon sources. Yield of PHB (expressed as weight % of dried cell mass) was determined by HPLC. Values represent averages of biological triplicates plus or minus the standard deviations about those averages. PHB was not detected in samples comprising the pMTL83157 (empty) plasmid.
Figure 4A:
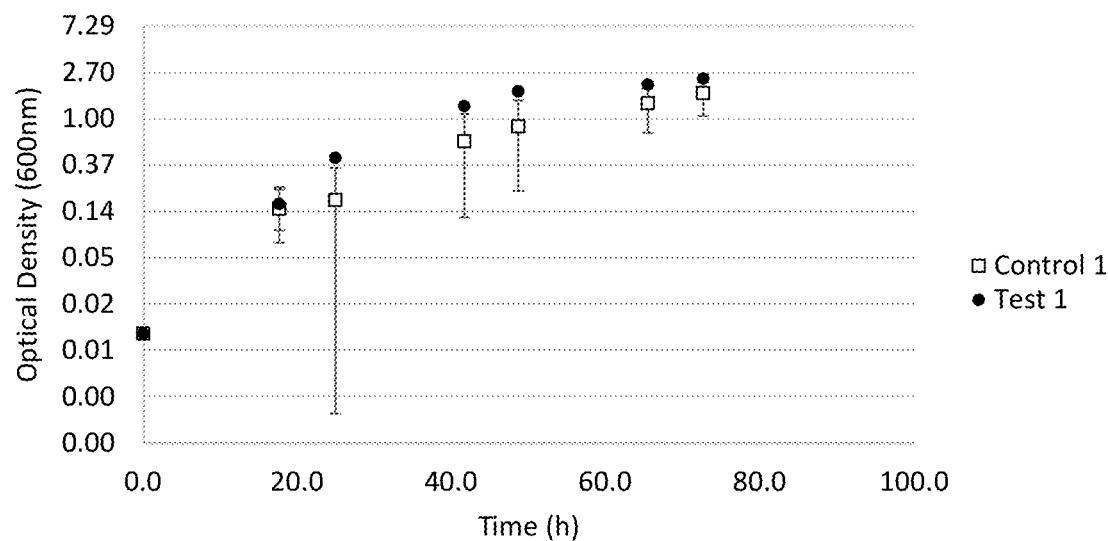
FIGS. 4A-4D are graphs showing growth of *C. autoethanogenum* under various growth conditions. Bacteria comprised either an empty plasmid (pMTL83157) or a plasmid comprising the PHB synthesis pathway (pPHB_01). Each plot represents a different set of conditions.
Figure 4B:
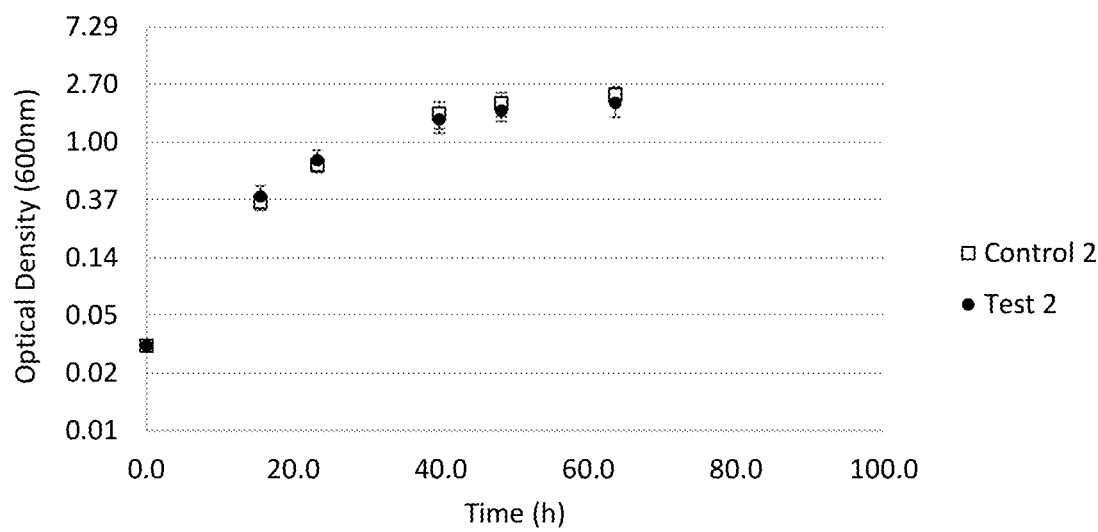
Figure 4C:
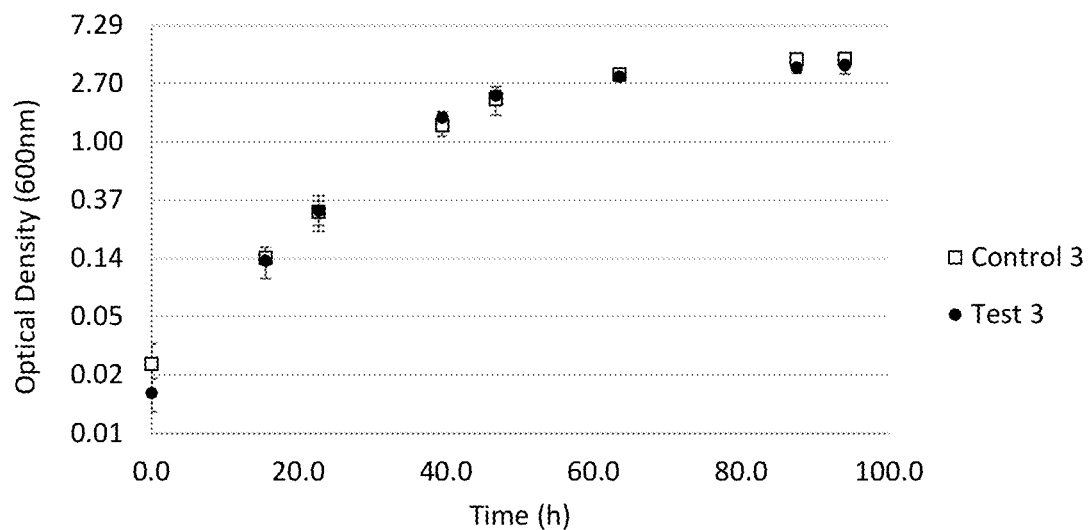
Figure 4D:
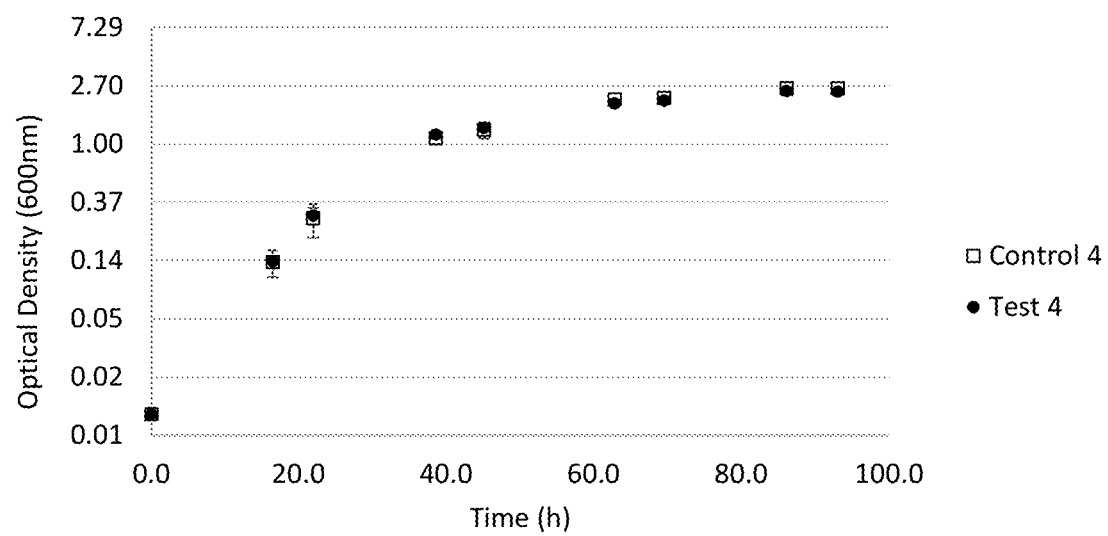

PHB yield was estimated by high-performance liquid chromatography (HPLC) in a similar manner as described elsewhere (Karr, *Appl Environ Microbiol*, 46, 1339-1344, 1983). Briefly, dried cells were treated with concentrated sulfuric acid and heated to convert the PHB to crotonic acid. Samples were cooled, diluted, filtered, and analyzed by HPLC with a UV-Vis detector to quantify the crotonic acid. The results of initial PHB production are summarized in FIG. 3, which shows the successful production of ~1.15 wt % PHB in a Wood-Ljungdahl microorganism.

However, given the low yields compared to native producers such as *Cupriavidus* and *Pseudomonas*, which are capable of synthesizing polymers like PHB such that they account for upwards of 90% of their weight, it appears that PHB synthesis from gas in Wood-Ljungdahl microorganisms is not nearly as simple as in native producers growing on non-gaseous substrates. Without wishing to be bound by any particular theory, the inventors postulate that PHB production in Wood-Ljungdahl microorganisms may require codon-adaptation to overcome the differences in pH preference, oxygen requirements, substrate utilizations, etc. between Wood-Ljungdahl microorganisms and native PHB producers.

After achieving synthesis of PHB in *C. autoethanogenum* from gaseous substrates, the work described above was repeated with altered growth conditions in an effort to explore for conditions that may favor/improve PHB yield. In particular, experiments were performed to repeat the conditions described above (condition 1, FIG. 4A), to change the gas composition to 50/30/10/10 $CO/CO_2/H_2/N_2$ (condition 2, FIG. 4B), to extend the incubation of the culture into stationary phase (condition 3, FIG. 4C), and to periodically refresh the gas in the bottles (condition 4, FIG. 4D). As shown in FIGS. 4A-4D, growth was similar for both the engineered strain and the control strain under all tested conditions.

Figure 5:
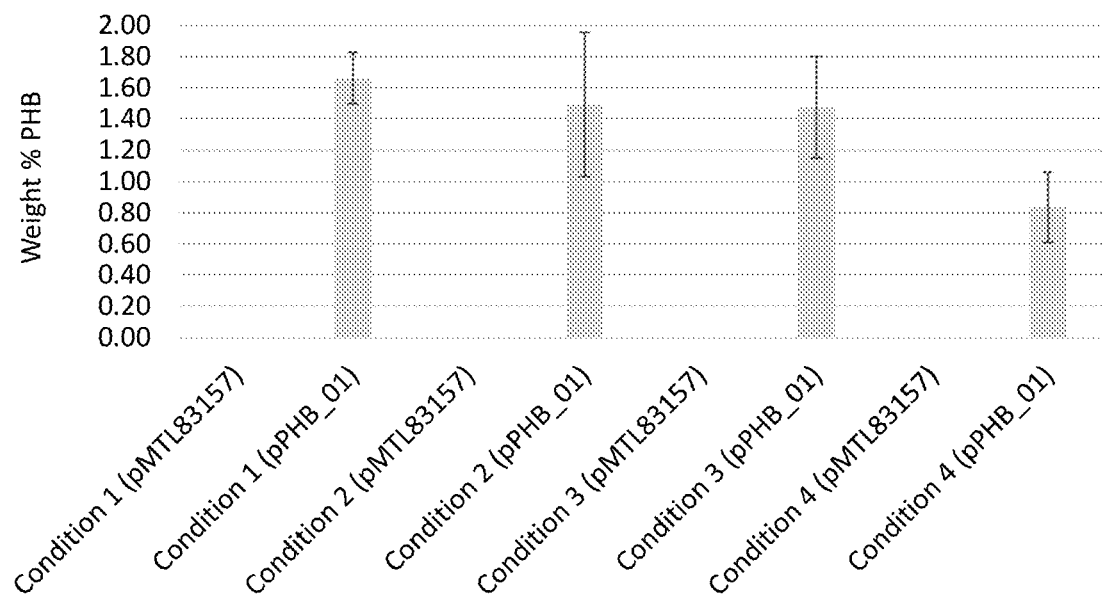
FIG. 5 is a graph showing PHB production in *C. autoethanogenum* under conditions 1-4, as described in connection with FIGS. 4A-4D. Values represent averages of biological triplicates plus or minus the standard deviations about those averages. PHB was not detected in samples comprising the pMTL83157 (empty) plasmid.

Cells were harvested and analyzed for PHB production as described above. The results are depicted in FIG. 5, which shows production of ~1.65 wt % PHB under condition 1, ~1.50 wt % PHB under condition 2, ~1.50 wt % PHB under condition 3, and ~0.85 wt % PHB under condition 4.

Example 3

This example demonstrates the production of PHB from gaseous substrates in a continuous fermentation.

The strain constructed in Example 1 was tested under continuous fermentation using gas as the main source of carbon, under conditions similar to those described in Valgepea, *Cell Syst.*, 4: 505-515, 2017. Similar to the experiments performed in Schott bottles, the continuous cultures were grown and handled anaerobically. Unlike the Schott bottles, the cultures were grown in a continuous fashion for approximately 20 days with constant feeding of media. Two different gas compositions were used for growth and PHB production: 50/20/20/10 $CO/CO_2/H_2/Ar$ and 50/20/2/28 $CO/CO_2/H_2/N_2$. Gas uptake was monitored using mass spectrometry (MS) and samples were taken periodically to quantify liquid metabolites by HPLC.

Figure 6:
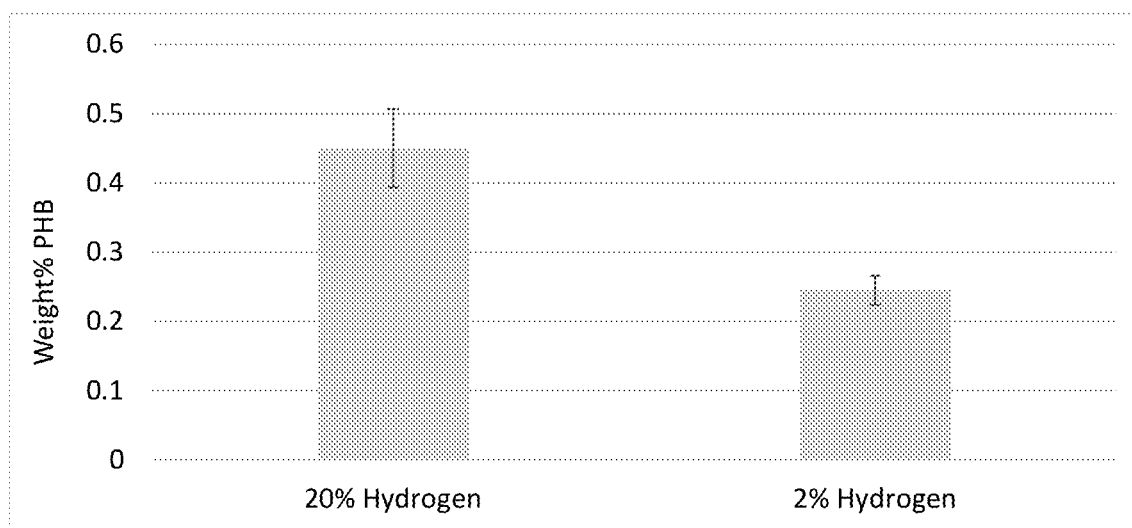
FIG. 6 is a graph showing PHB production in *C. autoethanogenum* from gaseous carbon sources in a continuous fermentation. The bacteria were conjugated with the plasmid pPHB_01 comprising a PHB synthesis pathway. PHB was measured at completion of the fermentation. Gas substrates comprised either 20% hydrogen or 2% hydrogen as part of their mixtures of 50/20/20/10 $CO/CO_2/H_2/Ar$ or 50/20/2/28 $CO/CO_2/H_2/N_2$, respectively. A pH of 5 was maintained. Values represent averages of duplicate fermentations plus or minus the standard deviations about those averages.

PHB was not quantified until completion of the continuous fermentation. Similar to the Schott bottle experiments, cells were collected by centrifugation, frozen, and dried by lyophilization. Dried cells were subsequently analyzed for PHB by treatment with sulfuric acid and heat to convert the PHB to crotonic acid. PHB quantification was then carried out via HPLC. Results of PHB production in the continuous fermentation are shown in FIG. 6. In particular, microorganisms grown on 20% hydrogen gas produced ~0.45 wt % PHB and microorganisms grown on 2% hydrogen gas produced ~0.25 wt % PHB.

Example 4

This example demonstrates fermenter optimization for increased PHB production.

Figure 7:
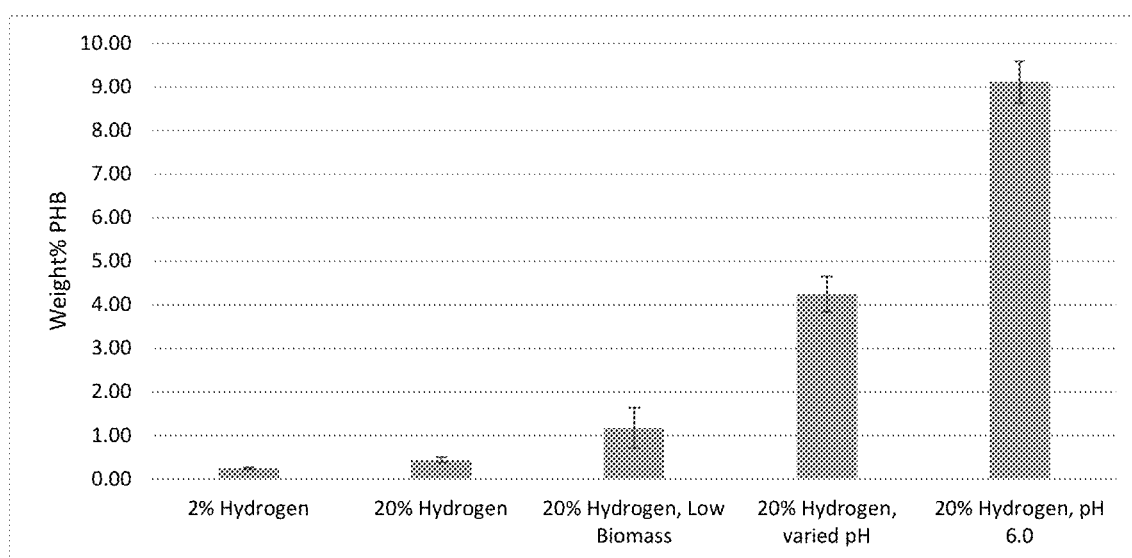
FIG. 7 is a graph showing enhanced PHB production in *C. autoethanogenum* from gaseous carbon sources in a continuous fermentation. The bacteria were conjugated with the plasmid pPHB_01 comprising a PHB synthesis pathway. PHB was measured at completion of the fermentation. Gas substrates comprised either 20% hydrogen or 2% hydrogen as part of their mixtures of 50/20/20/10 $CO/CO_2/H_2/Ar$ or 50/20/2/28 $CO/CO_2/H_2/N_2$, respectively. 20% hydrogen, low biomass had a decreased concentration of biomass compared to the other runs. 20% hydrogen, varied pH started with a pH of 6 and then reduced to 5.5. 20% hydrogen, pH 6 was maintained for the entirety of the fermentation run until cultures declined. Values represent averages of duplicate fermentations plus or minus the standard deviations about those averages.

Various conditions were tested within continuous fermentations to increase the PHB content in cells. Pools of acetyl-CoA and NADPH increase at lower biomass concentrations (Valgepea, *Cell Syst.*, 4: 505-515, 2017). Therefore, whether a lower steady-state biomass level would result in higher PHB through increased levels of the acetyl-CoA and NADPH pools was tested. Lowering the uptake rate of CO and, by extension, the biomass concentration in the fermenter, was shown to increase the flux of cellular resources toward PHB (FIG. 7).

Another factor found to increase PHB was pH. At higher pH, less acetic acid would diffuse and uncouple the proton motive force (PMF) (Valgepea, *Cell Syst.*, 4: 505-515, 2017). Therefore, whether increasing the pH from 5 to 5.5 or 6 would drain less energy for maintaining the PMF was tested. The extra available energy would provide additional ATP to support PHB production by reducing acetate production needed for ATP production. Changing the pH from 5.0 to 5.5 or 6.0 resulted in increased PHB production (~12.5 fold at pH 5.5). A pH value of 6.0, is difficult to maintain, however since *C. autoethanogenum* grows optimally at a more acidic pH.

Example 5

This example demonstrates changes to transcriptional and metabolome level when producing PHB, as compared to the control (empty plasmid) strain.

Analysis of transcriptome data from RNA sequencing was based on a previously published R-script (Valgepea, *Cell Syst.*, 4: 505-515, 2017) with the following modifications: use of the *C. autoethanogenum* NCBI reference sequence CP006763.1 and its annotated genome described in Brown, *Biotechnol. Biofuels*, 7: 40, 2014; addition of the nucleotide sequence for the three PHB genes (SEQ ID Nos: 3, 6, 9.)

A metabolomics package available in R (Livera and Bowne, R package, 2014) was used to perform the statistical analysis of the intracellular metabolomics data. This script normalizes and integrates the metabolomics data into a linear model fit (De Livera, *Anal. Chem.*, 84: 10768-10776, 2012). Intracellular metabolite concentrations were normalised per biomass (μmol/gDCW) prior to importing the data into the script. A linear model fit using ordinary statistics (i.e. non-Bayesian) was used for the statistical analysis of the metabolome data (De Livera, Anal. Chem., 84: 10768-10776, 2012; De Livera, Metabolomics Tools for Natual Product Discovery, 2013).

Although arginine was not supplied, an upregulation was observed for the arginine deiminase pathway, an alternative route found to provide ATP in acetogens (Valgepea, Metab. Eng. 41: 202-211, 2017) (q-value <0.01): arginine deiminase (CAETHG_3021, ~7 fold); ornithine carbamoyltransferase (CAETHG_3022, ~6 fold); carbamate kinase (CAETHG_3025, ~3.3 fold). Additionally, three genes encoding the Rnf complex, which is part of the energy conservation complex in acetogens (Schuchmann and Müller, Nat. Rev. Microbiol. 12: 809-821, 2014), showed an increase of ~2 fold in the PHB strain: (CAETHG_3231, q-value=0.02; CAETHG_3228, q-value=0.04 and CAETHG_3230, q-value=0.03). These observations highlight changes in energy metabolism due to the heterologous production. In addition, expression of two genes of the Wood-Ljungdahl pathway (WLP) encoding for the CO dehydrogenase/acetyl-CoA synthase (CAETHG_1610, ~1.4 fold; CAETHG_1611, ~1.2 fold) and a gene encoding a (FeFe)-hydrogenase (CAETHG_1691, ~2.5 fold) were upregulated in the PHB strain. These changes may reflect the increase needed for the production of acetyl-CoA and NADPH for PHB production (FIG. 1).

At the metabolome level, the PHB strain had a higher intracellular $NADH/NAD^+$ ratio compared to the EP. This suggests potential changes in the redox state after PHB expression. Production of acetate, the main native by-product of C. autoethanogenum metabolism (Abrini, Arch. Microbiol., 161: 345-351, 1994; Marcellin, Green Chem., 18: 3020-3028, 2016), decreased compared to the EP strain on syngas (p-value<0.01; two-tailed equal variance t-test). No change was observed on steel mill off gas.

Example 6

This example shows results of genome-scale metabolic model reconstructions (GEM). The genome-scale metabolic model GEM iCLAU786 (Valgepea, Cell Syst., 4: 505-515, 2017) was used with the addition of the PHB pathway. Simulations were performed for the PHB strain grown on syngas in all conditions listed above.

Flux simulations confirmed that less $CO_2$ was dissipated in the conditions with higher PHB (i.e. "Low biomass" and "pH5.5"). Additionally, as observed previously (Valgepea, Cell Syst., 4: 505-515, 2017), these simulations also showed that $CO_2$ was directly reduced to formate by $H_2$ through the formate-$H_2$ lyase activity of the electron-bifurcating hydrogenase-formate dehydrogenase (HytA-E/FdhA) enzyme complex (Wang, J. Bacteriol., 195: 4373-4386, 2013). This offers an advantage over the reduction of $CO_2$ by the redox-consuming formate dehydrogenase because no redox is consumed during $CO_2$ reduction in the WLP using the former enzyme complex. It was also observed that in the "Low biomass" and "pH5.5" experiments, balancing the total amount of reduced ferredoxin was achieved by either increasing or decreasing the flux to some key reactions, like the AOR (Aldehyde ferredoxin oxidoreductase), Nfn complex, or methylene THF reductase bifurcating reaction, compared to the control (PHB20).

Surprisingly, the "control" condition (PHB20) had, in silico, lower maintenance ATP cost (mmol/gDCW/h), and maintenance ATP costs from total ATP production (mATP %) compared to the "PHBpH5.5" condition.

Figure 8:
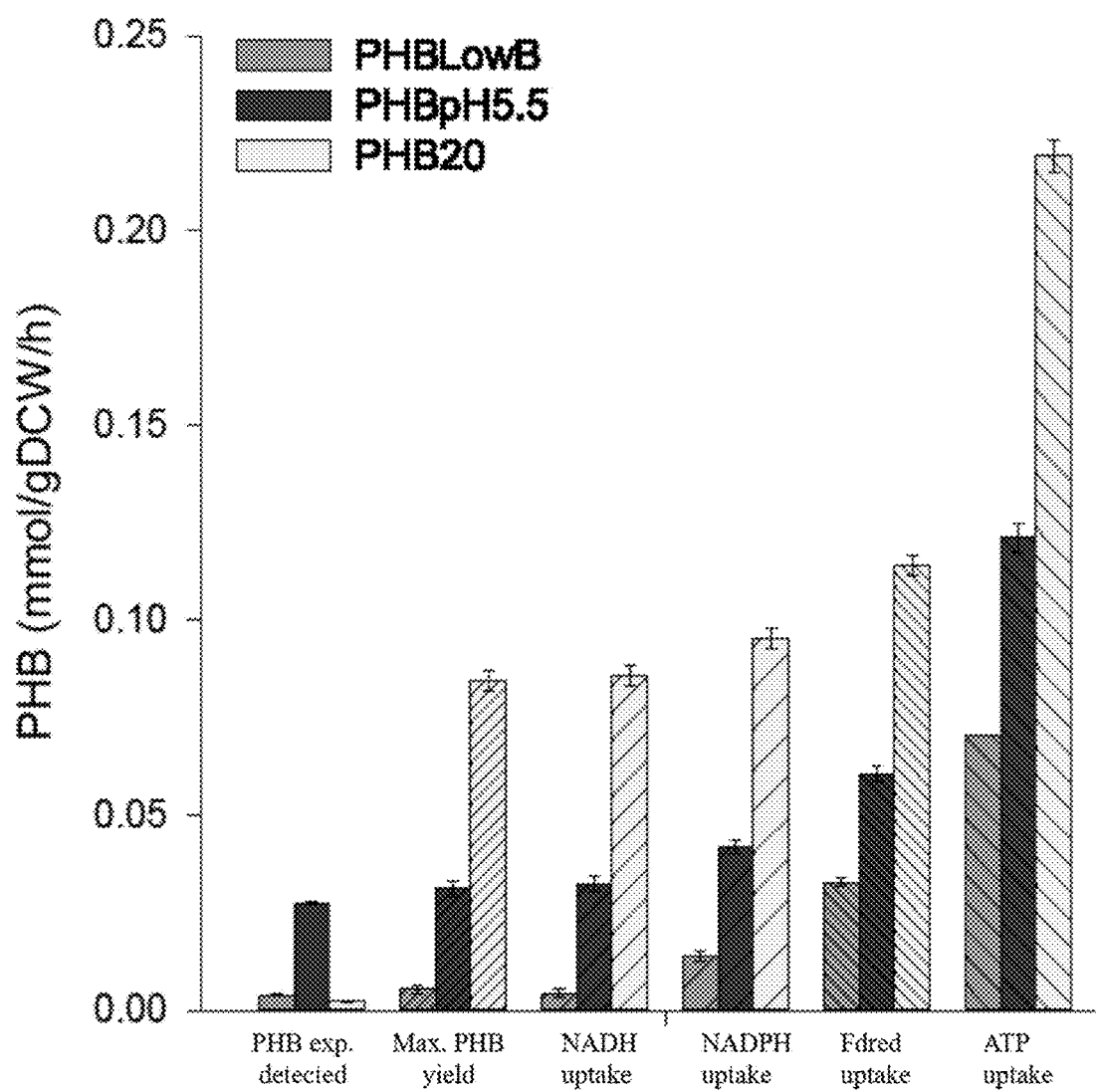
FIG. 8 is a graph showing PHB values for simulations using genome-scale metabolic model reconstructions (GEM). PHB experimentally detected was compared to the levels of PHB predicted by GEM using the maximization of PHB yield. Maximization of PHB yield was also tested with an uptake of 2 mmol/gDCW/h of either NADH, NADPH, $Fd_{red}$, or ATP. The conditions tested were PHB20 (control); PHBLowB (low biomass) and PHBpH5.5 (pH 5.5). ATP was found to be limiting PHB the most (highest PHB value achieved), followed by $Fd_{red}$, NADPH, and then NADH. Data represent an average±standard error of two biological replicates chemostats.

Simulations to determine if ATP, NADH, NADPH or reduced ferredoxin ($Fd_{red}$) was limiting PHB production were also run. The simulations showed that when ATP was provided, PHB production (mmol/gDCW/h) reached its maximum value among the "limiting" candidates in all conditions tested (i.e. "PHB20," "PHBLowBiomass," and "PHBpH5.5.") This observation is consistent with the understanding of acetogen metabolism being ATP-limited (Schuchmann and Müller, Nat. Rev. Microbiol. 12: 809-821, 2014). The model also showed that followed by the ATP limitation, PHB production is limited by $Fd_{red}$, NADPH, and then NADH availability (FIG. 8).

This result confirms the importance of ATP and $Fd_{red}$ as high energy carriers in acetogens. As ATP mostly supports anabolism and cellular maintenance, $Fd_{red}$ is essential for the Rnf energy conservation complex (Biegel, Cell. Mol. Life Sci. 68: 613-634, 2011) and only $Fd_{red}$ is known to provide electrons for the reduction of $CO_2$ to CO in the carbonyl branch of the WLP (Schuchmann and Müller, Nat. Rev. Microbiol. 12: 809-821, 2014).

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (e.g., "or") should be understood to mean either one, both, or any combination thereof of the alternatives. As used herein, the term "about" means±20% of the indicated range, value, or structure, unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A non-naturally occurring Wood-Ljungdahl microorganism capable of producing polyhydroxybutyrate comprising:
   a. a nucleic acid encoding a heterologous acetyl-CoA C-acetyltransferase (EC 2.3.1.9) enzyme that converts acetyl-CoA to acetoacetyl-CoA,
   b. a nucleic acid encoding a heterologous acetoacetyl-CoA reductase (EC 1.1.1.36) or a nucleic acid encoding a heterologous 3-hydroxybutyryl-CoA dehydrogenase (EC 1.1.1.157) enzyme that converts acetoacetyl-CoA to 3-hydroxybutyryl-CoA, and
   c. a nucleic acid encoding a heterologous polyhydroxyalkanoate synthase (EC 2.3.1.-) enzyme that converts 3-hydroxybutyryl-CoA to polyhydroxybutyrate.

2. The microorganism of claim 1, wherein the acetyl-CoA C-acetyltransferase is derived from a parental microorganism selected from the group consisting of *Acinetobacter baumannii, Aeromonas hydrophilia, Alcaligenes latus, Arthrospira platensis, Bacillus subtilis, Burkholderia cepacia, Clostridium acetobutylicum, Cupriavidus necator, Escherichia coli, Haloferax mediterranei, Pseudomonas aeruginosa, Pseudomonas fluorescens, Pseudomonas mandelii, Pseudomonas oleovorans, Pseudomonas putida*, and *Streptomyces coelicolor*.

3. The microorganism of claim 1, wherein the acetoacetyl-CoA reductase is derived from a parental microorganism selected from the group consisting of *Acinetobacter baumannii, Aeromonas hydrophilia, Alcaligenes latus, Arthrospira platensis, Bacillus subtilis, Burkholderia cepacia, Cupriavidus necator, Haloferax mediterranei, Pseudomonas aeruginosa, Pseudomonas fluorescens, Pseudomonas mandelii, Pseudomonas oleovorans, Pseudomonas putida*, and *Streptomyces coelicolor*.

4. The microorganism of claim 1, wherein the 3-hydroxybutyryl-CoA dehydrogenase is derived from *Clostridium beijerinckii, Clostridium acetobutylicum*, or *Clostridium kluyveri*.

5. The microorganism of claim 1, wherein the polyhydroxyalkanoate synthase is derived from a parental microorganism selected from the group consisting of *Acinetobacter baumannii, Aeromonas caviae, Aeromonas hydrophilia, Alcaligenes latus, Arthrospira platensis, Bacillus subtilis, Burkholderia cepacia, Cupriavidus necator, Haloferax mediterranei, Pseudomonas aeruginosa, Pseudomonas fluorescens, Pseudomonas mandelii, Pseudomonas oleovorans, Pseudomonas putida, Pseudomonas* sp. 61-3, *Rhodospirillum rubrum*, and *Streptomyces coelicolor*.

6. The microorganism of claim 1, wherein the microorganism is a member of a genus selected from the group consisting of *Acetobacterium, Alkalibaculum, Blautia, Butyribacterium, Clostridium, Eubacterium, Moorella, Oxobacter, Sporomusa*, and *Thermoanaerobacter*.

7. The microorganism of claim 1, wherein the microorganism is derived from a parental microorganism selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides*, and *Thermoanaerobacter kiuvi*.

8. The microorganism of claim 7, wherein the microorganism is derived from a parental bacterium selected from the group consisting of *Clostridium autoethanogenum, Clostridium coskatii, Clostridium ljungdahlii*, and *Clostridium ragsdalei*.

9. The microorganism of claim 1, wherein the microorganism consumes gaseous substrates comprising one or more of CO, $CO_2$, and $H_2$.

10. The microorganism of claim 1, wherein the microorganism is anaerobic.

11. The microorganism of claim 1, wherein the microorganism is not capable of degrading polyhydroxybutyrate.

12. The microorganism of claim 1, wherein the microorganism is not phototrophic, photosynthetic, or methanotrophic.

13. A method of producing polyhydroxybutyrate comprising culturing the microorganism of claim 1 in the presence of a gaseous substrate, whereby the microorganism produces polyhydroxybutyrate.

14. The method of claim 13, wherein the gaseous substrate comprises one or more of $CO$, $CO_2$, and $H_2$.

15. The method of claim 13, wherein the culturing is performed under anaerobic conditions.

16. The method of claim 13, wherein the culturing is performed in the absence of carbohydrate substrates.

17. The method of claim 13, wherein the culturing is performed in the absence of light.

* * * * *

SEQUENCE LISTING

<160> NUMBER OF SEQ ID NOS: 11

<210> SEQ ID NO 1
<211> LENGTH: 1179
<212> TYPE: DNA
<213> ORGANISM: Cupriavidus necator

<400> SEQUENCE: 1

```
atgactgacg ttgtcatcgt atccgccgcc cgcaccgcgg tcggcaagtt tggcggctcg    60
ctggccaaga tcccggcacc ggaactgggt gccgtggtca tcaaggccgc gctggagcgc   120
gccggcgtca agccggagca ggtgagcgaa gtcatcatgg ccaggtgct gaccgccggt    180 tcgggccaga accccgcacg ccaggccgcg atcaaggccg gcctgccggc gatggtgccg   240
gccatgacca tcaacaaggt gtgcggctcg ggcctgaagg ccgtgatgct ggccgccaac   300
gcgatcatgg cgggcgacgc cgagatcgtg gtggccggcg gccaggaaaa catgagcgcc   360
gccccgcacg tgctgccggg ctcgcgcgat ggtttccgca tgggcgatgc caagctggtc   420
gacaccatga tcgtcgacgg cctgtgggac gtgtacaacc agtaccacat gggcatcacc   480
gccgagaacg tggccaagga atacggcatc acacgcgagg cgcaggatga gttcgccgtc   540
ggctcgcaga acaaggccga agccgcgcag aaggccggca gtttgacga agagatcgtc    600 ccggtgctga tcccgcagcg caagggcgac ccggtggcct tcaagaccga cgagttcgtg   660
cgccagggcg ccacgctgga cagcatgtcc ggcctcaagc ccgccttcga caaggccggc   720
acggtgaccg cggccaacgc ctcgggcctg aacgacggcg ccgccgcggt ggtggtgatg   780
tcggcggcca aggccaagga actgggcctg accccgctgg ccacgatcaa gagctatgcc   840
aacgccggtc tcgatcccaa ggtgatgggc atgggccccg tgccggcctc caagcgcgcc   900
ctgtcgcgcg ccgagtggac cccgcaagac ctggacctga tggagatcaa cgaggccttt   960
gccgcgcagg cgctggcggt gcaccagcag atgggctggg acacctccaa ggtcaatgtg  1020
aacggcggcg ccatcgccat cggccacccg atcggcgcgt cgggctgccg tatcctggtg  1080
acgctgctgc acgagatgaa gcgccgtgac gcgaagaagg gcctggcctc gctgtgcatc  1140
ggcggcggca tgggcgtggc gctggcagtc gagcgcaaa                         1179
```

<210> SEQ ID NO 2
<211> LENGTH: 393
<212> TYPE: PRT
<213> ORGANISM: Cupriavidus necator

<400> SEQUENCE: 2

```
Met Thr Asp Val Val Ile Val Ser Ala Ala Arg Thr Ala Val Gly Lys
1               5                   10                  15

Phe Gly Gly Ser Leu Ala Lys Ile Pro Ala Pro Glu Leu Gly Ala Val
            20                  25                  30

Val Ile Lys Ala Ala Leu Glu Arg Ala Gly Val Lys Pro Glu Gln Val
        35                  40                  45

Ser Glu Val Ile Met Gly Gln Val Leu Thr Ala Gly Ser Gly Gln Asn
    50                  55                  60
```

Pro Ala Arg Gln Ala Ala Ile Lys Ala Gly Leu Pro Ala Met Val Pro
65                  70                  75                  80

Ala Met Thr Ile Asn Lys Val Cys Gly Ser Gly Leu Lys Ala Val Met
            85                  90                  95

Leu Ala Ala Asn Ala Ile Met Ala Gly Asp Ala Glu Ile Val Val Ala
            100                 105                 110

Gly Gly Gln Glu Asn Met Ser Ala Ala Pro His Val Leu Pro Gly Ser
            115                 120                 125

Arg Asp Gly Phe Arg Met Gly Asp Ala Lys Leu Val Asp Thr Met Ile
130                 135                 140

Val Asp Gly Leu Trp Asp Val Tyr Asn Gln Tyr His Met Gly Ile Thr
145                 150                 155                 160

Ala Glu Asn Val Ala Lys Glu Tyr Gly Ile Thr Arg Glu Ala Gln Asp
                165                 170                 175

Glu Phe Ala Val Gly Ser Gln Asn Lys Ala Glu Ala Ala Gln Lys Ala
            180                 185                 190

Gly Lys Phe Asp Glu Glu Ile Val Pro Val Leu Ile Pro Gln Arg Lys
            195                 200                 205

Gly Asp Pro Val Ala Phe Lys Thr Asp Glu Phe Val Arg Gln Gly Ala
210                 215                 220

Thr Leu Asp Ser Met Ser Gly Leu Lys Pro Ala Phe Asp Lys Ala Gly
225                 230                 235                 240

Thr Val Thr Ala Ala Asn Ala Ser Gly Leu Asn Asp Gly Ala Ala Ala
            245                 250                 255

Val Val Val Met Ser Ala Ala Lys Ala Lys Glu Leu Gly Leu Thr Pro
            260                 265                 270

Leu Ala Thr Ile Lys Ser Tyr Ala Asn Ala Gly Val Asp Pro Lys Val
            275                 280                 285

Met Gly Met Gly Pro Val Pro Ala Ser Lys Arg Ala Leu Ser Arg Ala
290                 295                 300

Glu Trp Thr Pro Gln Asp Leu Asp Leu Met Glu Ile Asn Glu Ala Phe
305                 310                 315                 320

Ala Ala Gln Ala Leu Ala Val His Gln Gln Met Gly Trp Asp Thr Ser
            325                 330                 335

Lys Val Asn Val Asn Gly Gly Ala Ile Ala Ile Gly His Pro Ile Gly
            340                 345                 350

Ala Ser Gly Cys Arg Ile Leu Val Thr Leu Leu His Glu Met Lys Arg
            355                 360                 365

Arg Asp Ala Lys Lys Gly Leu Ala Ser Leu Cys Ile Gly Gly Gly Met
370                 375                 380

Gly Val Ala Leu Ala Val Glu Arg Lys
385                 390

<210> SEQ ID NO 3
<211> LENGTH: 1182
<212> TYPE: DNA
<213> ORGANISM: Artificial sequence
<220> FEATURE:
<223> OTHER INFORMATION: Synthetic nucleic acid

<400> SEQUENCE: 3
atgactgatg tagtaatagt atctgcagca agaacggcag ttggaaaatt tggaggatct    60
ttggctaaaa tacctgcacc agaactaggg gcagtggtta taaaagcagc actggaaagg   120
gccggcgtca aaccagaaca ggtttcagaa gtaattatgg acaagttttt aacagctgga   180

```
tcaggtcaga atcctgcaag acaagcagct attaaagcag gacttccagc aatggtgcca      240
gctatgacca taaataaggt ttgtggcagt ggattaaagg cagtaatgtt ggcagctaat      300
gcaataatgg caggtgatgc agaaatagtt gtagcaggtg gtcaagaaaa tatgtctgct      360
gcaccacatg tactgccggg atctagggat ggttttagga tgggagatgc aaaattggtg      420
gatacaatga tagtagatgg actttgggat gtatacaatc agtatcacat gggaattaca      480
gctgaaaatg ttgctaaaga atatggaata actagaaag ctcaagatga gtttgcagta       540
ggttcacaaa ataaggctga agcagcacaa aaagccggaa atttgatga ggaaatagtt       600 cctgtattaa taccacaaag aaaaggagat cctgtagcat ttaaaacaga tgaatttgta      660
cgccagggag ctacattgga ttcaatgtct ggcttaaaac cggcctttga taaggcaggt      720
actgtaactg cagctaatgc aagtgggtta aatgatggag cagcagcagt tgtggtaatg      780
tcagcagcta agctaaaga gttgggtctt actccacttg caactataaa gagctatgca       840
aatgcaggag tcgatccaaa ggtcatgggc atgggtcctg ttccagcgtc taaaagagca      900
ctaagtagag ctgaatggac accacaagac ctggatctta tggaaataaa tgaagcattt      960
gctgcgcagg cccttgctgt ccatcaacaa atgggatggg atacttcaaa agtaaatgtg     1020
aatggaggag ctattgccat agggcatccc attggagcca gtggatgccg catttagta      1080 actttacttc atgagatgaa aagaagagat gcaaaaaag gacttgccag cttatgtata      1140
ggtggaggaa tgggtgtagc tttagccgtt gaaagaaaat aa                         1182

<210> SEQ ID NO 4
<211> LENGTH: 741
<212> TYPE: DNA
<213> ORGANISM: Cupriavidus necator

<400> SEQUENCE: 4
atgactcagc gcattgcgta tgtgaccggc ggcatggggg gtatcggaac cgccatttgc       60
cagcggctgg ccaaggatgg cttcgtgtgt gtggccggtt gcggcccaa ctcgccgcgc       120 cgcgaaaagt ggctggagca gcagaaggcc ctgggcttcg atttcattgc ctcggaaggc      180
aatgtggctg actgggactc gaccaagacc gcattcgaca aggtcaagtc cgaggtcggc      240
gaggttgatg tgctgatcaa caacgccggt atcacccgcg acgtggtgtt ccgcaagatg      300
acccgcgccg actgggatgc ggtgatcgac accaacctga cctcgctgtt caacgtcacc      360
aagcaggtga tcgacggcat ggccgaccgt ggctggggcc gcatcgtcaa catctcgtcg      420
gtgaacgggc agaagggcca gttcggccag accaactact ccaccgccaa ggccggcctg      480
catggcttca ccatggcact ggcgcaggaa gtggcgacca agggcgtgac cgtcaacacg      540
gtctctccgg gctatatcgc caccgacatg gtcaaggcga tccgccagga cgtgctcgac      600
aagatcgtcg cgacgatccc ggtcaagcgc ctgggcctgc cggaagagat cgcctcgatc      660
tgcgcctggt tgtcgtcgga ggagtccggt tcctcgaccg cgccgacttt ctcgctcaac      720
ggcggcctgc atatgggctg a                                                741

<210> SEQ ID NO 5
<211> LENGTH: 246
<212> TYPE: PRT
<213> ORGANISM: Cupriavidus necator

<400> SEQUENCE: 5

Met Thr Gln Arg Ile Ala Tyr Val Thr Gly Gly Met Gly Gly Ile Gly
1               5                   10                  15
```

Thr Ala Ile Cys Gln Arg Leu Ala Lys Asp Gly Phe Arg Val Val Ala
            20                  25                  30

Gly Cys Gly Pro Asn Ser Pro Arg Glu Lys Trp Leu Glu Gln Gln
        35                  40                  45

Lys Ala Leu Gly Phe Asp Phe Ile Ala Ser Glu Gly Asn Val Ala Asp
50                  55                  60

Trp Asp Ser Thr Lys Thr Ala Phe Asp Lys Val Lys Ser Glu Val Gly
65                  70                  75                  80

Glu Val Asp Val Leu Ile Asn Asn Ala Gly Ile Thr Arg Asp Val Val
                85                  90                  95

Phe Arg Lys Met Thr Arg Ala Asp Trp Asp Ala Val Ile Asp Thr Asn
            100                 105                 110

Leu Thr Ser Leu Phe Asn Val Thr Lys Gln Val Ile Asp Gly Met Ala
            115                 120                 125

Asp Arg Gly Trp Gly Arg Ile Val Asn Ile Ser Ser Val Asn Gly Gln
130                 135                 140

Lys Gly Gln Phe Gly Gln Thr Asn Tyr Ser Thr Ala Lys Ala Gly Leu
145                 150                 155                 160

His Gly Phe Thr Met Ala Leu Ala Gln Glu Val Ala Thr Lys Gly Val
                165                 170                 175

Thr Val Asn Thr Val Ser Pro Gly Tyr Ile Ala Thr Asp Met Val Lys
            180                 185                 190

Ala Ile Arg Gln Asp Val Leu Asp Lys Ile Val Ala Thr Ile Pro Val
            195                 200                 205

Lys Arg Leu Gly Leu Pro Glu Glu Ile Ala Ser Ile Cys Ala Trp Leu
            210                 215                 220

Ser Ser Glu Glu Ser Gly Phe Ser Thr Gly Ala Asp Phe Ser Leu Asn
225                 230                 235                 240

Gly Gly Leu His Met Gly
                245

<210> SEQ ID NO 6
<211> LENGTH: 741
<212> TYPE: DNA
<213> ORGANISM: Artificial sequence
<220> FEATURE:
<223> OTHER INFORMATION: Synthetic nucleic acid

<400> SEQUENCE: 6
atgacacaga gaatagctta tgtaactgga ggaatggggg gaattggcac ggcaatatgt      60
cagagattag caaaggatgg ttttagagta gttgcgggtt gtggcccaaa ctcaccgagg     120
agagaaaaat ggttggaaca gcagaaagct ctcggatttg actttatagc tagtgagggt     180
aatgttgctg attgggattc aacaaagaca gcttttgata aggttaagtc agaagtgggt     240
gaagtagatg tgctcataaa taatgctggg atcacaagag atgtagtttt tagaaaaatg     300
acaagagctg actgggatgc tgtaatagat acaaatctta ctagcttatt caatgtaacg     360
aaacaggtta tagatggaat ggcagatagg ggatgggta ggatagtaaa tatttcatca     420
gtaaatggtc aaaaggaca atttggacaa acaaattatt caactgccaa ggcaggactt     480
catggattta cgatggcact tgcacaggaa gtagctacta aggagttac tgtaaataca     540 gtttctccag atacatagc tactgatatg gtaaagcta ttaggcagga tgtattagat     600
aagattgtag caacaatacc tgtgaagaga cttggcttac tgaagaaat agcatcaata     660 tgtgcttggt tatccagtga agaatcagga ttttctacag gagctgattt ctccttgaat     720

```
ggtggacttc acatgggata a                                          741
```

<210> SEQ ID NO 7
<211> LENGTH: 1770
<212> TYPE: DNA
<213> ORGANISM: Cupriavidus necator

<400> SEQUENCE: 7

```
atggcgaccg gcaaaggcgc ggcagcttcc acgcaggaag gcaagtccca accattcaag    60
gtcacgccgg ggccattcga tccagccaca tggctggaat ggtcccgcca gtggcagggc   120
actgaaggca acgccacgc ggccgcgtcc ggcattccgg gcctggatgc gctggcaggc   180
gtcaagatcg cgccggcgca gctgggtgat atccagcagc gctacatgaa ggacttctca   240
gcgctgtggc aggccatggc cgagggcaag gccgaggcca ccgtccgct gcacgaccgg   300
cgcttcgccg cgacgcatg cgcaccaac ctcccatatc gcttcgctgc cgcgttctac    360
ctgcccaatg cgcgcgcctt gaccgagctg gccgatgccg tcgaggccga tgccaagacc   420
cgccagcgca tccgcttcgc gatctcgcaa tgggtcgatg cgatgtcgcc cgccaacttc   480
cttgccacca atcccgaggc gcagcgcctg ctgatcgagt cgggcggcga atcgctgcgt   540
gccggcgtgc gcaacatgat ggaagacctg acacgcggca agatctcgca gaccgacgag   600
agcgcgtttg aggtcggccg caatgtcgcg gtgaccgaag cgccgtggt cttcgagaac    660
gagtacttcc agctgttgca gtacaagccg ctgaccgaca aggtgcacgc gcgcccgctg   720
ctgatggtgc cgccgtgcat caacaagtac tacatcctgg acctgcagcc ggagagctcg   780
ctggtgcgcc atgtggtgga gcagggacat acggtgtttc tggtgtcgtg cgcaatccg    840
gacgccagca tggccggcag cacctgggac gactacatcg agcacgcggc catccgcgcc   900
atcgaagtcg cgcgcgacat cagcggccag gacaagatca acgtgctcgg cttctgcgtg   960
ggcggcacca ttgtctcgac cgcgctggcg gtgctggccg cgcgcggcga gcacccggcc  1020
gccagcgtca cgctgctgac cacgctgctg gactttgccg acacgggcat cctcgacgtc  1080
tttgtcgacg agggccatgt gcagttcgcg gaggccacgc tgggcggcgg cgccggcgcg  1140
ccgtgcgcgc tgctgcgcgg ccttgagctg gccaatacct tctcgttctt gcgcccgaac  1200
gacctggtgt ggaactacgt ggtcgacaac tacctgaagg gcaacacgcc ggtgccgttc  1260
gacctgctgt tctggaacgg cgacgccacc aacctgccgg gccgtggta ctgctggtac   1320
ctgcgccaca cctacctgca gaacgagctc aaggtaccgg gcaagctgac cgtgtgcggc  1380
gtgccggtgg acctggccag catcgacgtg ccgacctata tctacggctc gcgcgaagac  1440
catatcgtgc cgtggaccgc ggcctatgcc tcgaccgcgc tgctggcgaa caagctgcgc  1500
ttcgtgctgg tgcgtcggg ccatatcgcc ggtgtgatca cccgccggc caagaacaag   1560
cgcagccact ggactaacga tgcgctgccg gagtcgccgc agcaatggct ggccggcgcc  1620
atcgagcatc acggcagctg gtggccggac tggaccgcat ggctgccggg caggccggc   1680
gcgaaacgcg ccgcgcccgc caactatggc aatgcgcgct atcgcgcaat cgaacccgcg  1740
cctgggcgat acgtcaaagc caaggcatga                                  1770
```

<210> SEQ ID NO 8
<211> LENGTH: 588
<212> TYPE: PRT
<213> ORGANISM: Cupriavidus necator

<400> SEQUENCE: 8

-continued

```
Met Ala Thr Gly Lys Gly Ala Ala Ser Thr Gln Glu Gly Lys Ser
1               5                   10                  15

Gln Pro Phe Lys Val Thr Pro Gly Pro Phe Asp Pro Ala Thr Trp Leu
                20                  25                  30

Glu Trp Ser Arg Gln Trp Gln Gly Thr Glu Gly Asn Gly His Ala Ala
            35                  40                  45

Ala Ser Gly Ile Pro Gly Leu Asp Ala Leu Ala Gly Val Lys Ile Ala
        50                  55                  60

Pro Ala Gln Leu Gly Asp Ile Gln Gln Arg Tyr Met Lys Asp Phe Ser
65                  70                  75                  80

Ala Leu Trp Gln Ala Met Ala Glu Gly Lys Ala Glu Ala Thr Gly Pro
                85                  90                  95

Leu His Asp Arg Arg Phe Ala Gly Asp Ala Trp Arg Thr Asn Leu Pro
                100                 105                 110

Tyr Arg Phe Ala Ala Ala Phe Tyr Leu Leu Asn Ala Arg Ala Leu Thr
                115                 120                 125

Glu Leu Ala Asp Ala Val Glu Ala Asp Ala Lys Thr Arg Gln Arg Ile
            130                 135                 140

Arg Phe Ala Ile Ser Gln Trp Val Asp Ala Met Ser Pro Ala Asn Phe
145                 150                 155                 160

Leu Ala Thr Asn Pro Glu Ala Gln Arg Leu Leu Ile Glu Ser Gly Gly
                165                 170                 175

Glu Ser Leu Arg Ala Gly Val Arg Asn Met Met Glu Asp Leu Thr Arg
                180                 185                 190

Gly Lys Ile Ser Gln Thr Asp Glu Ser Ala Phe Glu Val Gly Arg Asn
            195                 200                 205

Val Ala Val Thr Glu Gly Ala Val Phe Glu Asn Glu Tyr Phe Gln
            210                 215                 220

Leu Leu Gln Tyr Lys Pro Leu Thr Asp Lys Val His Ala Arg Pro Leu
225                 230                 235                 240

Leu Met Val Pro Pro Cys Ile Asn Lys Tyr Tyr Ile Leu Asp Leu Gln
                245                 250                 255

Pro Glu Ser Ser Leu Val Arg His Val Val Glu Gln Gly His Thr Val
                260                 265                 270

Phe Leu Val Ser Trp Arg Asn Pro Asp Ala Ser Met Ala Gly Ser Thr
                275                 280                 285

Trp Asp Asp Tyr Ile Glu His Ala Ala Ile Arg Ala Ile Glu Val Ala
        290                 295                 300

Arg Asp Ile Ser Gly Gln Asp Lys Ile Asn Val Leu Gly Phe Cys Val
305                 310                 315                 320

Gly Gly Thr Ile Val Ser Thr Ala Leu Ala Val Leu Ala Ala Arg Gly
                325                 330                 335

Glu His Pro Ala Ala Ser Val Thr Leu Leu Thr Thr Leu Leu Asp Phe
                340                 345                 350

Ala Asp Thr Gly Ile Leu Asp Val Phe Val Asp Glu Gly His Val Gln
            355                 360                 365

Leu Arg Glu Ala Thr Leu Gly Gly Ala Gly Ala Pro Cys Ala Leu
        370                 375                 380

Leu Arg Gly Leu Glu Leu Ala Asn Thr Phe Ser Phe Leu Arg Pro Asn
385                 390                 395                 400

Asp Leu Val Trp Asn Tyr Val Val Asp Asn Tyr Leu Lys Gly Asn Thr
                405                 410                 415

Pro Val Pro Phe Asp Leu Leu Phe Trp Asn Gly Asp Ala Thr Asn Leu
```

```
            420                 425                 430
Pro Gly Pro Trp Tyr Cys Trp Tyr Leu Arg His Thr Tyr Leu Gln Asn
        435                 440                 445

Glu Leu Lys Val Pro Gly Lys Leu Thr Val Cys Gly Val Pro Val Asp
        450                 455                 460

Leu Ala Ser Ile Asp Val Pro Thr Tyr Ile Tyr Gly Ser Arg Glu Asp
465                 470                 475                 480

His Ile Val Pro Trp Thr Ala Ala Tyr Ala Ser Thr Ala Leu Leu Ala
                485                 490                 495

Asn Lys Leu Arg Phe Val Leu Gly Ala Ser Gly His Ile Ala Gly Val
            500                 505                 510

Ile Asn Pro Pro Ala Lys Asn Lys Arg Ser His Trp Thr Asn Asp Ala
        515                 520                 525

Leu Pro Glu Ser Pro Gln Gln Trp Leu Ala Gly Ala Ile Glu His His
        530                 535                 540

Gly Ser Trp Trp Pro Asp Trp Thr Ala Trp Leu Ala Gly Gln Ala Gly
545                 550                 555                 560

Ala Lys Arg Ala Ala Pro Ala Asn Tyr Gly Asn Ala Arg Tyr Arg Ala
                565                 570                 575

Ile Glu Pro Ala Pro Gly Arg Tyr Val Lys Ala Lys
            580                 585

<210> SEQ ID NO 9
<211> LENGTH: 1767
<212> TYPE: DNA
<213> ORGANISM: Artificial sequence
<220> FEATURE:
<223> OTHER INFORMATION: Synthetic nucleic acid

<400> SEQUENCE: 9
atggctacag gaaaaggagc agcagctagt acacaggaag gaaaatcaca accgtttaaa      60
gttacaccag gtccttttga cccagccacc tggttagaat ggtcacgcca gtggcagggt     120
actgagggaa atggacatgc agcagcaagt ggcattccag gattggatgc tcttgctggg     180
gtaaagatag ctccagctca gcttggagat atacaacaga gatatatgaa agattttttca    240 gctctttggc aagccatggc agaaggaaaa gcagaagcga caggtccact tcatgacaga     300
agatttgctg agatgcttg gagaaactaat ttgccatata gatttgctgc cgcttttttat    360 cttttgaatg ccagagctttt aactgagctt gcagatgctg tagaagctga tgctaaaaca    420
agacagagaa taagatttgc tatttcccaa tgggttgatg ctatgtcgcc ggcgaatttt     480
ttagctacaa atcctgaggc acagagatta cttattgagt ccggaggaga atcactaagg     540
gctggagtga gaaatatgat ggaagatttg accagaggaa agatctctca gacagacgaa     600
tctgcatttg aagtaggaag aatgttgcg gtaactgaag gtgctgttgt atttgaaaat      660
gaatattttc aattactaca atataaacct tgacagaca aggtgcatgc tagacctctt      720
cttatggttc caccttgtat aaataaatat tatattttag atcttcagcc tgaatcatct     780
ttagtaagac acgttgtaga acaaggtcac acagtatttt agtttccttg agaaatcct     840 gacgcatcta tggccggcag tacctgggat gattatatag aacatgcagc aataagggca    900
atagaagttg ctagagatat aagcggtcag acaagatta atgtacttgg attttgtgta    960
ggaggaacta gttttcaac agcactggca gtattggctg ctagaggaga acatccagca    1020
gcatcggtaa ctttacttac aacactttta gattttgcag atactggaat attagacgta    1080
tttgttgatg aaggacacgt acaattaaga gaggcaacct gggtggagg agctggtgca    1140
```

```
ccctgtgctc ttcttagagg gttagaatta gcaaatactt ttagtttttt acgacctaat    1200
gacttagttt ggaattatgt agtggataat taccttaaag gaaacacacc tgtacctttt    1260
gatttattat tttggaatgg agatgcaacc aacttgcctg gtccttggta ttgttggtat    1320
cttagacata cctaccttca aaatgaatta aaagttcctg gcaaactcac tgtatgcggt    1380
gtccccgttg atttggcttc aatagatgta ccaacttata tatacggaag tagagaggat    1440
catatcgtac cttggactgc ggcttacgct tctacagcat tgctggctaa taaattgaga    1500
tttgtattag gagcttctgg tcacatagct ggagtaataa atccaccagc caaaaataaa    1560
cgaagtcatt ggaccaatga tgcacttcct gaatctccac agcagtggct tgctggtgca    1620
atagaacatc atggttcatg gtggcccgac tggacagcat ggttggcagg tcaagccggt    1680
gctaaaaggg ctgcgccagc aaactatggc aatgcaagat acagggctat agaaccggct    1740
ccaggaagat acgttaaagc aaaataa                                       1767
```

<210> SEQ ID NO 10
<211> LENGTH: 5024
<212> TYPE: DNA
<213> ORGANISM: Artificial sequence
<220> FEATURE:
<223> OTHER INFORMATION: Synthetic nucleic acid

<400> SEQUENCE: 10

```
cctgcaggat aaaaaattg tagataaatt ttataaaata gttttatcta caatttttt      60 atcaggaaac agctatgacc gcggccgcag atagtcataa tagttccaga atagttcaat    120
ttagaaatta gactaaactt caaaatgttt gttaaatata taccaaaacta gtatagatat    180 tttttaaata ctggacttaa acagtagtaa tttgcctaaa aaattttttc aattttttt     240 aaaaaatcct tttcaagttg tacattgtta tggtaatatg taattgaaga agttatgtag    300
taatattgta aacgtttctt gattttttta catccatgta gtgcttaaaa aaccaaaata    360
tgtcacatgc aattgtatat ttcaaataac aatatttatt ttctcgttaa attcacaaat    420
aatttattaa taatatcaat aaccaagatt atacttaaat ggatgtttat ttttaacac     480 ttttatagta aatatattta ttttatgtag taaaaaggtt ataattataa ttgtatttat    540
tacaattaat taaaataaaa ataggttttt aggtaaaatt aagttatttt aagaagtaat    600
tacaataaaa attgaagtta ttgctttaag gagggaatta ttcatatgac catgattacg    660
aattcgagct cggtacccgg ggatcctcta gagtcgacgt cacgcgtcca tggagatctc    720
gaggcctgca gacatgcaag cttggcactg gccgtcgttt tacaacgtcg tgactgggaa    780
aaccctggcg ttacccaact taatcgcctt gcagcacatc ccctttcgc cagctggcgt     840 aatagcgaag aggcccgcac cgatcgccct tcccaacagt tgcgcagcct gaatggcgaa    900
tggcgctagc ataaaaataa gaagcctgca tttgcaggct tcttattttt atggcgcgcc    960
gccattattt ttttgaacaa ttgacaattc atttcttatt ttttattaag tgatagtcaa    1020
aaggcataac agtgctgaat agaaagaaat ttacagaaaa gaaaattata gaatttagta    1080
tgattaatta tactcattta tgaatgttta attgaataca aaaaaaaata cttgttatgt    1140
attcaattac gggttaaaat atagacaagt tgaaaaattt aataaaaaaa taagtcctca    1200
gctcttatat attaagctac caacttagta tataagccaa aacttaaatg tgctaccaac    1260
acatcaagcc gttagagaac tctatctata gcaatatttc aaatgtaccg acatacaaga    1320
gaaacattaa ctatatatat tcaatttatg agattatctt aacagatata aatgtaaatt    1380
```

```
gcaataagta agatttagaa gtttatagcc tttgtgtatt ggaagcagta cgcaaaggct    1440 ttttttatttg ataaaaatta gaagtatatt tattttttca taattaattt atgaaaatga   1500 aaggggggtga gcaaagtgac agaggaaagc agtatcttat caaataacaa ggtattagca   1560
atatcattat tgactttagc agtaaacatt atgactttta tagtgcttgt agctaagtag    1620
tacgaaaggg ggagctttaa aaagctcctt ggaatacata gaattcataa attaatttat    1680
gaaaagaagg gcgtatatga aaacttgtaa aaattgcaaa gagtttatta agatactga    1740 aatatgcaaa atacattcgt tgatgattca tgataaaaca gtagcaacct attgcagtaa    1800
atacaatgag tcaagatgtt tacataaagg gaaagtccaa tgtattaatt gttcaaagat    1860
gaaccgatat ggatggtgtg ccataaaaat gagatgtttt acagaggaag aacagaaaaa    1920
agaacgtaca tgcattaaat attatgcaag gagctttaaa aaagctcatg taaagaagag    1980 taaaagaaa aaataattta tttattaatt taatattgag agtgccgaca cagtatgcac     2040
taaaaaatat atctgtggtg tagtgagccg atacaaaagg atagtcactc gcattttcat    2100
aatacatctt atgttatgat tatgtgtcgg tgggacttca cgacgaaaac ccacaataaa    2160
aaaagagttc ggggtagggt taagcatagt tgaggcaact aaacaatcaa gctaggatat    2220
gcagtagcag accgtaaggt cgttgtttag gtgtgttgta atacatacgc tattaagatg    2280
taaaaatacg gataccaatg aagggaaaag tataattttt ggatgtagtt tgtttgttca    2340
tctatgggca aactacgtcc aaagccgttt ccaaatctgc taaaaagtat atcctttcta    2400
aaatcaaagt caagtatgaa atcataaata aagtttaatt ttgaagttat tatgatatta    2460
tgtttttcta ttaaaataaa ttaagtatat agaatagttt aataatagta tatacttaat    2520
gtgataagtg tctgacagtg tcacagaaag gatgattgtt atggattata agcggccggc    2580
cagtgggcaa gttgaaaaat tcacaaaaat gtggtataat atctttgttc attagagcga    2640
taaacttgaa tttgagaggg aacttagatg gtatttgaaa aaattgataa aaatagttgg    2700
aacagaaaag agtattttga ccactacttt gcaagtgtac cttgtaccta cagcatgacc    2760
gttaaagtgg atatcacaca aataaaggaa aagggaatga aactatatcc tgcaatgctt    2820
tattatattg caatgattgt aaaccgccat tcagagttta ggacggcaat caatcaagat    2880
ggtgaattgg ggatatatga tgagatgata ccaagctata caatatttca caatgatact    2940
gaaacatttt ccagcctttg gactgagtgt aagtctgact ttaaatcatt tttagcagat    3000
tatgaaagtg atacgcaacg gtatggaaac aatcatagaa tggaaggaaa gccaaatgct    3060
ccggaaaaca ttttttaatgt atctatgata ccgtggtcaa ccttcgatgg ctttaatctg    3120
aatttgcaga aaggatatga ttatttgatt cctattttta ctatggggaa atattataaa    3180
gaagataaca aaattatact tcctttggca attcaagttc atcacgcagt atgtgacgga    3240
tttcacattt gccgttttgt aaacgaattg caggaattga taaatagtta acttcaggtt    3300
tgtctgtaac taaaaacaag tatttaagca aaaacatcgt agaaatacgg tgttttttgt    3360 tacccctaagt ttaaactcct tttttgataat ctcatgacca aaatcccctta acgtgagttt   3420 tcgttccact gagcgtcaga ccccgtagaa aagatcaaag gatcttcttg agatcctttt    3480
tttctgcgcg taatctgctg cttgcaaaca aaaaaaccac cgctaccagc ggtggttttgt   3540 ttgccggatc aagagctacc aactctttttt ccgaaggtaa ctggcttcag cagagcgcag    3600
ataccaaata ctgttcttct agtgtagccg tagttaggcc accacttcaa gaactctgta    3660
gcaccgccta catacctcgc tctgctaatc ctgttaccag tggctgctgc cagtggcgat    3720
aagtcgtgtc ttaccgggtt ggactcaaga cgatagttac cggataaggc gcagcggtcg    3780
```

```
ggctgaacgg ggggttcgtg cacacagccc agcttggagc gaacgaccta caccgaactg    3840
agatacctac agcgtgagct atgagaaagc gccacgcttc ccgaagggag aaaggcggac    3900
aggtatccgg taagcggcag ggtcggaaca ggagagcgca cgagggagct tccaggggga    3960
aacgcctggt atctttatag tcctgtcggg tttcgccacc tctgacttga gcgtcgattt    4020
ttgtgatgct cgtcaggggg gcggagccta tggaaaaacg ccagcaacgc ggccttttta    4080
cggttcctgg cctttttgct gccttttgct cacatgttct ttcctgcgtt atcccctgat    4140
tctgtggata accgtattac cgcctttgag tgagctgata ccgctcgccg cagccgaacg    4200
accgagcgca gcgagtcagt gagcgaggaa gcggaagagc gcccaatacg cagggccccc    4260
tgcttcgggg tcattatagc gattttttcg gtatatccat cctttttcgc acgatataca    4320
ggattttgcc aaagggttcg tgtagacttt ccttggtgta tccaacggcg tcagccgggc    4380
aggataggtg aagtaggccc acccgcgagc gggtgttcct tcttcactgt cccttattcg    4440 cacctggcg tgctcaacgg gaatcctgct ctgcgaggct ggccggctac cgccggcgta    4500
acagatgagg gcaagcggat ggctgatgaa accaagccaa ccaggaaggg cagcccacct    4560
atcaaggtgt actgccttcc agacgaacga gagcgattg aggaaaaggc ggcggcggcc    4620
ggcatgagcc tgtcggccta cctgctggcc gtcggccagg gctacaaaat cacgggcgtc    4680
gtggactatg agcacgtccg cgagctgccc gcatcaatg cgacctggg ccgcctgggc    4740 ggcctgctga actctggct caccgacgac ccgcgcacgg cgcggttcgg tgatgccacg    4800
atcctcgccc tgctggcgaa gatcgaagag aagcaggacg agcttggcaa ggtcatgatg    4860
ggcgtggtcc gcccgagggc agagccatga ctttttttagc cgctaaaacg gccgggggt    4920 gcgcgtgatt gccaagcacg tccccatgcg ctccatcaag aagagcgact tcgcggagct    4980
ggtgaagtac atcaccgacg agcaaggcaa gaccgatcgg gccc                    5024

<210> SEQ ID NO 11
<211> LENGTH: 8765
<212> TYPE: DNA
<213> ORGANISM: Artificial sequence
<220> FEATURE:
<223> OTHER INFORMATION: Synthetic nucleic acid

<400> SEQUENCE: 11
cctgcaggat aaaaaaattg tagataaatt ttataaaata gttttatcta caatttttttt      60 atcaggaaac agctatgacc gcggccgcag atagtcataa tagttccaga atagttcaat     120
ttagaaatta gactaaactt caaaatgttt gttaaatata taccaaacta gtatagatat     180
tttttaaata ctggacttaa acagtagtaa tttgcctaaa aaattttttc aattttttttt    240 aaaaaatcct tttcaagttg tacattgtta tggtaatatg taattgaaga agttatgtag     300
taatattgta aacgtttctt gattttttta catccatgta gtgcttaaaa accaaaata      360 tgtcacatgc aattgtatat ttcaaataac aatatttatt ttctcgttaa attcacaaat     420
aatttattaa taatatcaat aaccaagatt atacttaaat ggatgtttat tttttaacac     480
ttttatagta aatatattta tttttatgtag taaaaaggtt ataattataa ttgtatttat    540
tacaattaat taaaataaaa atagggtttt aggtaaaatt aagttatttt aagaagtaat     600
tacaataaaa attgaagtta ttgctttaag gagggaatta ttcatatggc tacaggaaaa     660
ggagcagcag ctagtacaca ggaaggaaaa tcacaaccgt ttaaagttac accaggtcct     720
tttgacccag ccacctggtt agaatggtca cgccagtggc agggtactga gggaaatgga     780
```

-continued

```
catgcagcag caagtggcat ccaggattg gatgctcttg ctggggtaaa gatagctcca    840
gctcagcttg gagatataca acagagatat atgaaagatt tttcagctct ttggcaagcc    900
atggcagaag gaaaagcaga agcgacaggt ccacttcatg acagaagatt tgctggagat    960
gcttggagaa ctaatttgcc atatagattt gctgccgctt tttatctttt gaatgccaga   1020
gctttaactg agcttgcaga tgctgtagaa gctgatgcta aaacaagaca gagaataaga   1080
tttgctattt cccaatgggt tgatgctatg tcgccggcga attttttagc tacaaatcct   1140
gaggcacaga gattacttat tgagtccgga ggagaatcac taagggctgg agtgagaaat   1200
atgatggaag atttgaccag aggaaagatc tctcagacag acgaatctgc atttgaagta   1260
ggaaggaatg ttgcggtaac tgaaggtgct gttgtatttg aaaatgaata ttttcaatta   1320
ctacaatata aacctttgac agacaaggtg catgctagac ctcttcttat ggttccacct   1380
tgtataaata aatattatat tttagatctt cagcctgaat catctttagt aagacacgtt   1440
gtagaacaag gtcacacagt attttttagtt tcttggagaa atcctgacgc atctatggcc   1500
ggcagtacct gggatgatta tatagaacat gcagcaataa gggcaataga agttgctaga   1560
gatataagcg gtcaggacaa gattaatgta cttggatttt tgtgtaggagg aactatagtt   1620 tcaacagcac tggcagtatt ggctgctaga ggagaacatc cagcagcatc ggtaacttta   1680
cttacaacac ttttagattt tgcagatact ggaatattag acgtatttgt tgatgaagga   1740
cacgtacaat aagagaggc aaccttgggt ggaggagctg gtgcaccctg tgctcttctt   1800
agagggttag aattagcaaa tacttttagt ttttttacgac ctaatgactt agtttggaat   1860
tatgtagtgg ataattaccct taaggaaac acacctgtac cttttgattt attattttgg   1920
aatggagatg caaccaactt gcctggtcct tggtattgtt ggtatcttag acatacctac   1980
cttcaaaatg aattaaaagt tcctggcaaa ctcactgtat gcggtgtccc cgttgatttg   2040
gcttcaatag atgtaccaac ttatatatac ggaagtagag aggatcatat cgtaccttgg   2100
actgcggctt acgcttctac agcattgctg gctaataaat tgagatttgt attaggagct   2160
tctggtcaca tagctggagt aataaatcca ccagccaaaa ataaacgaag tcattggacc   2220
aatgatgcac ttcctgaatc tccacagcag tggcttgctg gtgcaataga acatcatggt   2280
tcatggtggc ccgactggac agcatggttg gcaggtcaag ccggtgctaa aagggctgcg   2340
ccagcaaact atggcaatgc aagatacagg gctatagaac cggctccagg aagatacgtt   2400
aaagcaaaat aagaattcga gctcggtacc aggaggatat taaaatgact gatgtagtaa   2460
tagtatctgc agcaagaacg gcagttggaa aatttggagg atctttggct aaaataccctg   2520 caccagaact agggggcagtg gttataaaag cagcactgga aagggccggc gtcaaaccag   2580
aacaggtttc agaagtaatt atgggacaag ttttaacagc tggatcaggt cagaatcctg   2640
caagacaagc agctattaaa gcaggacttc cagcaatggt gccagctatg accataaata   2700
aggtttgtgg cagtggatta aaggcagtaa tgttggcagc taatgcaata atggcaggtg   2760
atgcagaaat agttgtagca ggtggtcaag aaaatatgtc tgctgcacca catgtactgc   2820
cgggatctag ggatggtttt aggatgggag atgcaaaatt ggtggataca atgatagtag   2880
atggactttg ggatgtatac aatcagtatc acatgggaat tacagctgaa atgttgcta   2940 aagaatatgg aataactaga gaagctcaag atgagtttgc agtaggttca caaaataagg   3000
ctgaagcagc acaaaaagcc ggaaaatttg atgaggaaat agttcctgta ttaataccac   3060
aaagaaaagg agatcctgta gcatttaaaa cagatgaatt tgtacgccag ggagctcat   3120 tggattcaat gtctggctta aaaccggcct ttgataaggc aggtactgta actgcagcta   3180
```

```
atgcaagtgg gttaaatgat ggagcagcag cagttgtggt aatgtcagca gctaaagcta    3240
aagagttggg tcttactcca cttgcaacta taaagagcta tgcaaatgca ggagtcgatc    3300
caaaggtcat gggcatgggt cctgttccag cgtctaaaag agcactaagt agagctgaat    3360
ggacaccaca agacctggat cttatggaaa taaatgaagc atttgctgcg caggcccttg    3420
ctgtccatca acaaatggga tgggatactt caaaagtaaa tgtgaatgga ggagctattg    3480
ccatagggca tcccattgga gccagtggat gccgcatttt agtaacttta cttcatgaga    3540
tgaaaagaag agatgcaaaa aaggacttg ccagcttatg tataggtgga ggaatgggtg    3600
tagctttagc cgttgaaaga aaataaatca ttctgaattc gagctcggta ggaggtcaga    3660
atgacacaga gaatagctta tgtaactgga ggaatggggg gaattggcac ggcaatatgt    3720
cagagattag caaggatgg ttttagagta gttgcgggtt gtggcccaaa ctcaccgagg    3780
agagaaaaat ggttggaaca gcagaaagct ctcggatttg actttatagc tagtgagggt    3840
aatgttgctg attgggattc aacaaagaca gcttttgata aggttaagtc agaagtgggt    3900
gaagtagatg tgctcataaa taatgctggg atcacaagag atgtagtttt tagaaaaatg    3960
acaagagctg actgggatgc tgtaatagat acaaatctta ctagcttatt caatgtaacg    4020
aaacaggtta tagatggaat ggcagatagg ggatggggta ggatagtaaa tatttcatca    4080
gtaaatggtc aaaaggaca atttggacaa acaaattatt caactgccaa ggcaggactt    4140
catggattta cgatggcact tgcacaggaa gtagctacta aggagttac tgtaaataca    4200 gtttctccag gatacatagc tactgatatg gtaaaagcta ttaggcagga tgtattagat    4260
aagattgtag caacaatacc tgtgaagaga cttggcttac ctgaagaaat agcatcaata    4320
tgtgcttggt tatccagtga agaatcagga ttttctacag gagctgattt ctccttgaat    4380
ggtggacttc acatgggata aaattcgagc tcggtacccg gggatcctct agagtcgacg    4440
tcacgcgtcc atggagatct cgaggcctgc agacatgcaa gcttggcact ggccgtcgtt    4500
ttacaacgtc gtgactggga aaaccctggc gttacccaac ttaatcgcct tgcagcacat    4560
ccccctttcg ccagctggcg taatagcgaa gaggcccgca ccgatcgccc ttcccaacag    4620
ttgcgcagcc tgaatggcga atggcgctag cataaaaata gaagcctgc atttgcaggc    4680 ttcttatttt tatggcgcgc cgccattatt tttttgaaca attgacaatt catttcttat    4740
tttttattaa gtgatagtca aaaggcataa cagtgctgaa tagaaagaaa tttacagaaa    4800
agaaaattat agaatttagt atgattaatt atactcattt atgaatgttt aattgaatac    4860
aaaaaaaaat acttgttatg tattcaatta cgggttaaaa tatagacaag ttgaaaaatt    4920
taataaaaaa ataagtcctc agctcttata tattaagcta ccaacttagt atataagcca    4980
aaacttaaat gtgctaccaa cacatcaagc cgttagagaa ctctatctat agcaatattt    5040
caaatgtacc gacatacaag agaaacatta actatatata ttcaatttat gagattatct    5100
taacagatat aaatgtaaat tgcaataagt aagatttaga agtttatagc ctttgtgtat    5160
tggaagcagt acgcaaaggc ttttttattt gataaaaatt agaagtatat ttatttttc    5220 ataattaatt tatgaaaatg aaaggggtg agcaaagtga cagaggaaag cagtatctta    5280
tcaaataaca aggtattagc aatatcatta ttgactttag cagtaaacat tatgactttt    5340
atagtgcttg tagctaagta gtacgaaagg gggagcttta aaaagctcct tggaatacat    5400
agaattcata aattaattta tgaaaagaag ggcgtatatg aaaacttgta aaaattgcaa    5460
agagtttatt aaagatactg aaatatgcaa aatacattcg ttgatgattc atgataaaac    5520
```

```
agtagcaacc tattgcagta aatacaatga gtcaagatgt ttacataaag ggaaagtcca    5580
atgtattaat tgttcaaaga tgaaccgata tggatggtgt gccataaaaa tgagatgttt    5640
tacagaggaa gaacagaaaa aagaacgtac atgcattaaa tattatgcaa ggagctttaa    5700
aaaagctcat gtaaagaaga gtaaaagaa aaataattt atttattaat ttaatattga    5760
gagtgccgac acagtatgca ctaaaaaata tatctgtggt gtagtgagcc gatacaaaag    5820
gatagtcact cgcattttca taatacatct tatgttatga ttatgtgtcg gtgggacttc    5880
acgacgaaaa cccacaataa aaaagagtt cggggtaggg ttaagcatag ttgaggcaac    5940
taaacaatca agctaggata tgcagtagca gaccgtaagg tcgttgttta ggtgtgttgt    6000
aatacatacg ctattaagat gtaaaaatac ggataccaat gaagggaaaa gtataatttt    6060
tggatgtagt ttgtttgttc atctatgggc aaactacgtc caaagccgtt tccaaatctg    6120
ctaaaaagta tatcctttct aaaatcaaag tcaagtatga aatcataaat aaagtttaat    6180
tttgaagtta ttatgatatt atgttttct attaaaataa attaagtata tagaatagtt    6240
taataatagt atatacttaa tgtgataagt gtctgacagt gtcacagaaa ggatgattgt    6300
tatgattat aagcggccgg ccagtgggca agttgaaaaa ttcacaaaaa tgtggtataa    6360
tatctttgtt cattagagcg ataaacttga atttgagagg gaacttagat ggtatttgaa    6420
aaaattgata aaaatagttg gaacagaaaa gagtattttg accactactt tgcaagtgta    6480
ccttgtacct acagcatgac cgttaaagtg gatatcacac aaataaagga aaagggaatg    6540
aaactatatc ctgcaatgct ttattatatt gcaatgattg taaaccgcca ttcagagttt    6600
aggacggcaa tcaatcaaga tggtgaattg gggatatatg atgagatgat accaagctat    6660
acaatatttc acaatgatac tgaaacattt tccagccttt ggactgagtg taagtctgac    6720
tttaaatcat ttttagcaga ttatgaaagt gatacgcaac ggtatggaaa caatcataga    6780
atggaaggaa agccaaatgc tccggaaaac atttttaatg tatctatgat accgtggtca    6840
accttcgatg gctttaatct gaatttgcag aaaggatatg attatttgat tcctattttt    6900
actatgggga atattataa agaagataac aaaattatac ttcctttggc aattcaagtt    6960
catcacgcag tatgtgacgg atttcacatt tgccgttttg taaacgaatt gcaggaattg    7020
ataaatagtt aacttcaggt ttgtctgtaa ctaaaaacaa gtatttaagc aaaaacatcg    7080
tagaaatacg gtgttttttg ttaccctaag tttaaactcc ttttttgataa tctcatgacc    7140
aaaatcccctt aacgtgagtt ttcgttccac tgagcgtcag accccgtaga aaagatcaaa    7200
ggatcttctt gagatccttt ttttctgcgc gtaatctgct gcttgcaaac aaaaaaacca    7260
ccgctaccag cggtggtttg tttgccggat caagagctac caactctttt tccgaaggta    7320
actggcttca gcagagcgca gataccaaat actgttcttc tagtgtagcc gtagttaggc    7380
caccacttca agaactctgt agcaccgcct acatacctcg ctctgctaat cctgttacca    7440
gtggctgctg ccagtggcga taagtcgtgt cttaccgggt tggactcaag acgatagtta    7500
ccggataagg cgcagcggtc gggctgaacg ggggggttcgt gcacacagcc agcttggag    7560
cgaacgacct acaccgaact gagataccta cagcgtgagc tatgagaaag cgccacgctt    7620
cccgaaggga gaaggcgga caggtatccg gtaagcggca gggtcggaac aggagagcgc    7680
acgagggagc ttccaggggg aaacgcctgg tatctttata gtcctgtcgg gtttcgccac    7740
ctctgacttg agcgtcgatt tttgtgatgc tcgtcagggg ggcggagcct atggaaaaac    7800
gccagcaacg cggcctttttt acggttcctg gccttttgct ggccttttgc tcacatgttc    7860
tttcctgcgt tatcccctga ttctgtggat aaccgtatta ccgcctttga gtgagctgat    7920
```

```
accgctcgcc gcagccgaac gaccgagcgc agcgagtcag tgagcgagga agcggaagag    7980
cgcccaatac gcagggcccc ctgcttcggg gtcattatag cgattttttc ggtatatcca    8040 tccttttcg cacgatatac aggattttgc caaagggttc gtgtagactt tccttggtgt     8100
atccaacggc gtcagccggg caggataggt gaagtaggcc cacccgcgag cgggtgttcc    8160
ttcttcactg tcccttattc gcacctggcg gtgctcaacg ggaatcctgc tctgcgaggc    8220
tggccggcta ccgccggcgt aacagatgag ggcaagcgga tggctgatga aaccaagcca    8280
accaggaagg gcagcccacc tatcaaggtg tactgccttc cagacgaacg aagagcgatt    8340
gaggaaaagg cggcggcggc cggcatgagc ctgtcggcct acctgctggc cgtcggccag    8400
ggctacaaaa tcacgggcgt cgtggactat gagcacgtcc gcgagctggc ccgcatcaat    8460
ggcgacctgg gccgcctggg cggcctgctg aaactctggc tcaccgacga cccgcgcacg    8520
gcgcggttcg gtgatgccac gatcctcgcc ctgctggcga agatcgaaga gaagcaggac    8580
gagcttggca aggtcatgat gggcgtggtc cgcccgaggg cagagccatg actttttag     8640 ccgctaaaac ggccggggg tgcgcgtgat tgccaagcac gtccccatgc gctccatcaa     8700
gaagagcgac ttcgcggagc tggtgaagta catcaccgac gagcaaggca agaccgatcg    8760
ggccc                                                                8765
```